United States Patent [19]
Ortyl et al.

[11] Patent Number: 5,855,912
[45] Date of Patent: Jan. 5, 1999

[54] PHARMACEUTICAL COMPOSITIONS FOR PIPERIDINALKANOL COMPOUNDS

[75] Inventors: Thomas T. Ortyl, Overland Park; Paul F. Skultety, Leawood, both of Kans.; Kristen C. Mitchell, Lee's Summit, Mo.; Deepak S. Phadke, Olathe, Kans.; Faraneh Attarchi, Kansas City, Mo.; Marguerite L. Pierce, Fairway, Kans.; Aaron W. Schoeneman, Lee's Summit; Joseph M. Schnitz, Kansas City, both of Mo.

[73] Assignee: Hoechst Marion Roussel, Inc., Cincinnati, Ohio

[21] Appl. No.: 943,460

[22] Filed: Oct. 3, 1997

Related U.S. Application Data

[63] Continuation of Ser. No. 552,287, Dec. 12, 1995, abandoned, which is a continuation-in-part of Ser. No. 395,952, Feb. 28, 1995, abandoned.

[51] Int. Cl.[6] .............................. A61K 9/20; A61K 9/48; A61K 47/36; A61K 47/38
[52] U.S. Cl. ........................ 424/452; 424/465; 514/777; 514/781
[58] Field of Search ...................... 424/452, 465; 514/777, 781

[56] References Cited

U.S. PATENT DOCUMENTS

| | | |
|---|---|---|
| 3,806,526 | 4/1974 | Carr et al. . |
| 3,878,217 | 4/1975 | Carr et al. . |
| 3,966,949 | 6/1976 | Webb et al. . |
| 3,979,520 | 9/1976 | Rothe et al. . |
| 4,060,634 | 11/1977 | Rothe et al. . |
| 4,196,188 | 4/1980 | Besins . |
| 4,254,129 | 3/1981 | Carr et al. . |
| 4,254,130 | 3/1981 | Carr et al. . |
| 4,285,957 | 8/1981 | Carr et al. . |
| 4,285,958 | 8/1981 | Carr et al. . |
| 4,609,675 | 9/1986 | Franz ...................................... 514/568 |
| 4,639,458 | 1/1987 | Katdare .................... 514/311 |
| 4,840,799 | 6/1989 | Appelgren et al. ..................... 424/493 |
| 4,916,163 | 4/1990 | Ni . |
| 4,929,605 | 5/1990 | Domet et al. .............................. 514/54 |
| 4,963,540 | 10/1990 | Maxon et al. . |
| 4,996,061 | 2/1991 | Webb et al. ............................. 424/475 |
| 4,999,226 | 3/1991 | Schock et al. .......................... 424/472 |
| 5,021,242 | 6/1991 | Romer et al. . |
| 5,049,568 | 9/1991 | Kristof . |
| 5,169,638 | 12/1992 | Dennis et al. . |
| 5,271,944 | 12/1993 | Lee . |
| 5,375,693 | 12/1994 | Woosley et al. ......................... 514/317 |
| 5,376,386 | 12/1994 | Ganderton . |
| 5,429,825 | 7/1995 | Reo et al. ................................ 424/490 |
| 5,472,704 | 12/1995 | Santus et al. ........................... 424/455 |
| 5,476,654 | 12/1995 | Conte et al. ......................... 424/78.08 |
| 5,487,901 | 1/1996 | Conte et al. ............................ 424/472 |
| 5,567,439 | 10/1996 | Myers et al. ............................ 424/456 |
| 5,587,172 | 12/1996 | Cherukuri et al. ...................... 424/401 |

FOREIGN PATENT DOCUMENTS

| | | |
|---|---|---|
| 0111114 | 10/1983 | European Pat. Off. . |
| 0173293 | 8/1985 | European Pat. Off. . |
| 396404 | 11/1990 | European Pat. Off. . |
| 468392 | 1/1992 | European Pat. Off. . |
| 582380 | 2/1994 | European Pat. Off. . |
| 636365 | 2/1995 | European Pat. Off. . |
| 9409761 | 5/1994 | WIPO . |
| 9501781 | 1/1995 | WIPO . |

OTHER PUBLICATIONS

Anderson et al PCT/WO 94 13271 Jun. 24, 1994.
Trofast et al EP 508969 (Oct. 1992).
Webb et al EP 311067 (Apr. 1989).
Gowan et al EP 636364 (Feb. 1995).
Hansen WO/PCT 93 17665 (Sep. 1993).
Akehurst et al WO/PCT 93 11744 (Jun. 1993).
Axelsson EP 260241 (Mar. 1988).
Leigh WO/PCT 87 07502 (Dec. 1987).
*Comprehensive Medicinal Chemistry*, vol. 5, Biopharmaceutics, pp. 563–566.

*Primary Examiner*—Shep K. Rose
*Attorney, Agent, or Firm*—Louis J. Wille

[57] ABSTRACT

The invention provides a pharmaceutical composition in solid unit dosage form, comprising, a) a therapeutically effective amount of a piperidinoalkanol compound or a pharmaceutically acceptable salt thereof; and, b) at least one inert ingredient.

25 Claims, No Drawings

PHARMACEUTICAL COMPOSITIONS FOR PIPERIDINALKANOL COMPOUNDS

CROSS-REFERENCE TO RELATED APPLICATION

This is a continuation of application Ser. No. 08/552,287, filed Dec. 12, 1995 now abandoned, which is a continuation-in-part of application Ser. No. 08/395,952, filed Feb. 28, 1995, now abandoned, which is herein incorporated by reference.

BACKGROUND OF THE INVENTION

It has been established that various piperidinoalkanol compounds are useful as antihistamines, antiallergy agents and bronchodilators as disclosed in U.S. Pat. Nos. 3,878,217, 4,254,129 and 4,285,957. Several examples of formulations of these various piperidinoalkanol compounds are described below.

In U.S. Pat. No. 4,929,605, J. Domet and D. Shah describe a pharmaceutical composition in solid unit dosage form, comprising, a therapeutically effective amount of a piperidinoalkanol compound, or a pharmaceutically acceptable salt thereof, a pharmaceutically acceptable nonionic or cationic surfactant in an amount of from about 0.1% to about 6% by weight of the composition, and a pharmaceutically acceptable carbonate salt in an amount of from about 2% to about 50% by weight of the composition.

N. Webb and G. Hammer describe in U.S. Pat. No. 4,996,061, a pharmaceutical composition in the form of a multiple-compression tablet comprising a discrete zone made from a formulation which provides sustained-release of a therapeutically effective decongestant amount of a sympathomimetic drug and a discrete zone made from a different formulation which provides immediate release of a therapeutically effective antihistaminic amount of a piperidinoalkanol and, optionally, a therapeutically effective decongestant amount of a sympathomimetic drug.

Efforts have focused on improving the bioavailability of various piperidinoalkanol compounds in order to improve their therapeutic efficiency. The present invention relates to pharmaceutical compositions and pharmaceutical compositions in solid unit dosage form wherein the piperidinoalkanol compound, or a pharmaceutically acceptable salt thereof, is in combination with inert ingredients.

SUMMARY OF THE INVENTION

The present invention provides a pharmaceutical composition in solid unit dosage form, comprising, a) a therapeutically effective amount of a piperidinoalkanol compound or a pharmaceutically acceptable salt thereof; and b) at least one inert ingredient.

The present invention further provides a pharmaceutical composition prepared by a wet granulation process comprising, preparing the wet granulation wherein a compound of the formula;

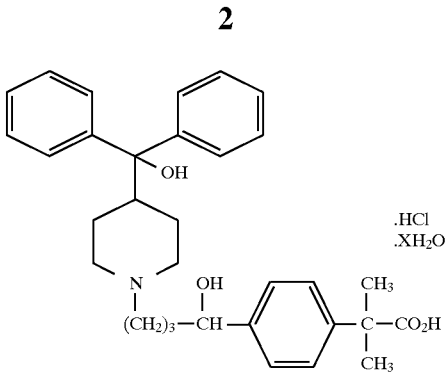

wherein X is a number ranging from about zero to 5, and the individual optical isomers thereof, a diluent and a disintegrant are mixed with a solution of a binding agent; the wet granulation is screened; and the wet granulation is dried. In addition, the present invention provides combining the above dry granulation with a lubricant. The present invention further provides pressing the above final mixture into a tablet.

DETAILED DESCRIPTION OF THE INVENTION

As used herein the terms "piperidinoalkanol compounds" and "piperidinoalkanol compounds and their pharmaceutically acceptable salts" refers to those compounds described by formulas (I), (II) and (III) which are disclosed in U.S. Pat. Nos. 3,878,217, 4,254,129 and 4,285,957 the disclosure of each patent being incorporated herein by reference. In addition, the patent application entitled "Pharmaceutical Composition Piperidinoalkanol Compounds', U.S. Pat. No. 08/395,952, filed Feb. 28, 1995 is incorporated herein by reference.

Piperidinoalkanol compounds of formula (I) are those which correspond to the formula;

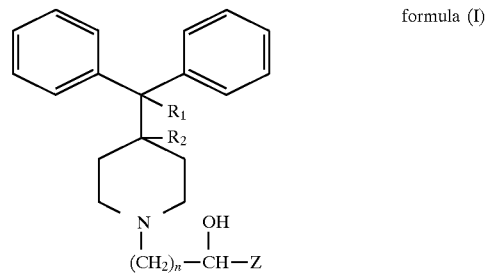

formula (I)

wherein $R_1$ is hydrogen or hydroxy; $R_2$ is hydrogen; or $R_1$ and $R_2$ taken together form a second bond between the carbon atoms bearing $R_1$ and $R_2$; n is a positive whole integer of from 1 to 3; Z is thienyl, phenyl or substituted phenyl wherein the substituents on the substituted phenyl may be attached at the ortho, meta or para positions of the unsubstituted phenyl ring and are selected from the group consisting of a halogen atom, a straight or branched lower alkyl chain of from 1 to 4 carbon atoms, a lower alkoxy group of from 1 to 4 carbon atoms, a di(lower)alkylamino group, or a saturated monocyclic heterocyclic ring selected from the group consisting of pyrolidino, piperidino, morpholino, or N-(lower)alkylpiperizino, or pharmaceutically acceptable acid addition salts thereof.

Piperidinoalkanol compounds of formula (II) are those which correspond to the formula;

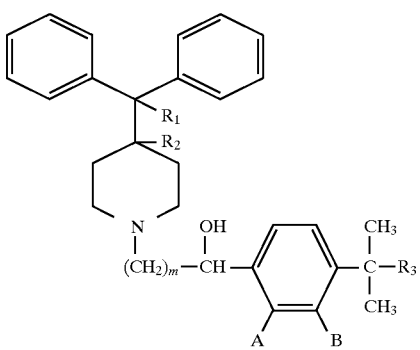

formula (II)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_3$ is —$CH_3$, or —$CH_2OH$; each A and B is hydrogen or hydroxy; with the provisos that at least one of A or B is hydrogen and one of A or B is other than hydrogen when $R_3$ is —$CH_3$; and pharmaceutically acceptable salts and individual optical isomers thereof.

Piperidinoalkanol compounds of formula (III) are those which correspond to the formula;

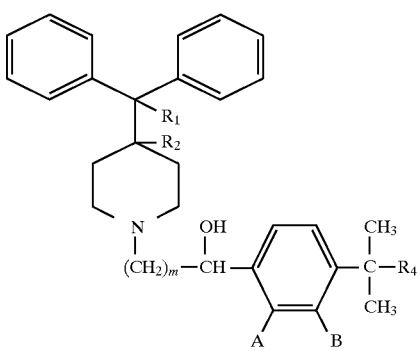

formula (III)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_4$ is —$CO_2H$ or —CO2alkyl wherein the alkyl moiety has from 1 to 6 carbon atoms and is straight or branched; each of A and B is hydrogen or hydroxy; with the proviso that at least one of A or B is hydrogen; and pharmaceutically acceptable salts and individual optical isomers thereof.

More specifically, 4-[4-[4-(Hydroxydiphenylmethyl)-1-piperdinyl]-1-hydroxybutyl]-α,α-dimethylbenzeneacetic acid hydrochloride of formula (IIIa)

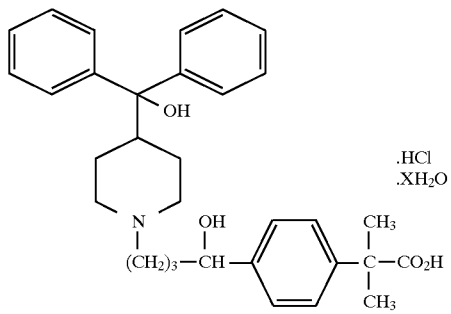

formula (IIIa)

wherein X is a number ranging from about zero to 5, and the individual optical isomers thereof, is a preferred piperidinoalkanol compound. The compound 4-[4-[4-(Hydroxydiphenylmethyl)-1-piperdinyl]-1-hydroxybutyl-α,α-dimethylbenzeneacetic acid hydrochloride wherein X is zero or one in formula (IIIa) is the most preferred piperidinoalkanol compound.

In addition, the free base of 4-[4-[4-(Hydroxydiphenylmethyl)-1-piperdinyl]-1-hydroxybutyl]-α,α-dimethylbenzeneacetic acid of formula (IIIb)

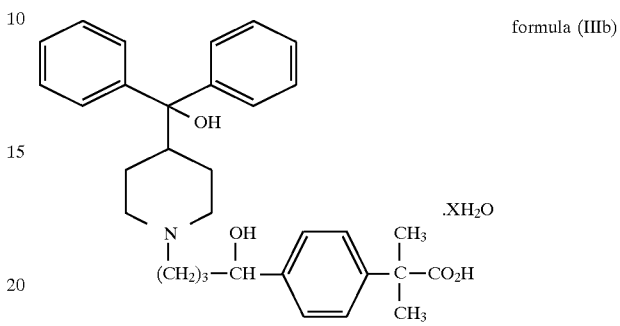

formula (IIIb)

wherein X is a number ranging from about zero to 5, and the individual optical isomers thereof, is also a preferred piperidinoalkanol compound.

Further included within the scope of the piperidinoalkanol compounds of formulas (III), (IIIa) and (IIIb) are the polymorphic, pseudomorphic and amorphous forms, and mixtures thereof. More specifically, the polymorphs of anhydrous 4-[4-[4-(Hydroxydiphenylmethyl)-1-piperidinyl]-1-hydroxybutyl]-α,α-dimethylbenzeneacetic acid hydrochloride which are designated herein as Form I and Form III. The Form I polymorph of anhydrous 4-[4-[4-(Hydroxydiphenylmethyl)-1-piperidinyl]-1-hydroxybutyl] α,α-dimethylbenzeneacetic acid hydrochloride may be identified by the following characteristics: a visual melting point (capillary tube) in the range of about 196°–201° C.; a melt endotherm with extrapolated onset in the range of about 195°–199° C. as determined by differential scanning calorimetry; and an X-ray powder diffraction pattern essentially as shown in Table 1 wherein the XRPD patterns were measured using a powder diffractometer equipped with a Co X-ray tube source. The sample was illuminated with Co $K\alpha_1$ radiation and XRPD data were collected from 5° to 55° 2θ. (intensities may vary radically due to preferred orientation).

TABLE 1

| D-Space, Angstroms | Intensity, $I/I_o$, % |
|---|---|
| 11.8 | 30 |
| 7.3 | 30 |
| 6.3 | 65 |
| 5.9 | 35 |
| 5.0 | 45 |
| 4.8 | 100 |
| 4.4 | 45 |
| 3.9 | 60 |
| 3.8 | 75 |
| 3.7 | 30 |

The Form III polymorph of anhydrous 4-[4-[4-(Hydroxydiphenylmethyl)-1-piperidinyl]-1-hydroxybutyl]-α,α-dimethylbenzeneacetic acid hydrochloride may be identified by the following characteristics: a visual melting point (capillary tube) in the range of about 166°–171° C.; a broad endotherm below about 90° C., a melt endotherm with an extrapolated onset of about 166° C. as determined by differential scanning calorimetry; and an X-ray powder diffraction pattern essentially as shown in Table 2 wherein the XRPD patterns were measured using a powder diffractometer equipped with a Co X-ray tube source. The sample was illuminated with Co K$\alpha_1$ radiation and XRPD data were collected from 5° to 55° 2θ (intensities may vary radically due to preferred orientation).

TABLE 2

| D-Space, Angstroms | Intensity, I/I$_o$, % |
| --- | --- |
| 9.0 | 95 |
| 4.9 | 100 |
| 4.8 | 35 |
| 4.6 | 25 |
| 4.5 | 25 |
| 3.7 | 25 |

In addition, the pseudomorphs of hydrated 4-[4-[4-(Hydroxydiphenylmethyl)-1-piperidinyl]-1-hydroxybutyl]-α,α-dimethylbenzeneacetic acid hydrochloride are designated herein as Form II and Form IV. The Form II pseudomorph of hydrated 4-[4-(4-(Hydroxydiphenylmethyl)-1-piperidinyl]-1-hydroxybutyl]-α,α-dimethylbenzeneacetic acid hydrochloride may be identified by the following characteristics: a visual melting point (capillary tube) in the range of about 100°–105° C.; a large broad endotherm below about 100° C. and a small endothermic peak (about 2 joules/gram) with extrapolated onsets in the range of about 124°–126° C. as determined by differential scanning calorimetry; and an X-ray powder diffraction pattern essentially as shown in Table 3 wherein the XRPD patterns were measured using a powder diffractometer equipped with a Co X-ray tube source. The sample was illuminated with Co K$\alpha_1$, radiation and XRPD data were collected from 5° to 55° 2θ. (intensities may vary radically due to preferred orientation).

TABLE 3

| D-Space, Angstroms | Intensity, I/I$_o$, % |
| --- | --- |
| 7.8 | 45 |
| 6.4 | 44 |
| 5.2 | 85 |
| 4.9 | 60 |
| 4.7 | 80 |
| 4.4 | 55 |
| 4.2 | 50 |
| 4.1 | 60 |
| 3.7 | 75 |
| 3.6 | 60 |
| 3.5 | 50 |

The Form IV pseudomorph of hydrated 4-[4-[4-(Hydroxydiphenylmethyl)-1-piperidinyl]-1-hydroxybutyl]-α,α-dimethylbenzeneacetic acid hydrochloride may be identified by the following characteristics: a visual melting point (capillary tube) in the range of about 113°–118° C.; two broad overlapping endotherms below about 100° C. and an additional endotherm with an extrapolated onset at approximately 146° C. as determined by differential scanning calorimetry and an X-ray powder diffraction pattern essentially as shown in Table 4 wherein the XRPD patterns were measured using a powder diffractometer equipped with a Co X-ray tube source. The sample was illuminated with Co K$\alpha_1$ radiation and XRPD data were collected from 5° to 55° 2θ (intensities may vary radically due to preferred orientation).

TABLE 4

| D-Space, Angstroms | Intensity, I/I$_o$, % |
| --- | --- |
| 10.4 | 60 |
| 7.0 | 45 |
| 6.4 | 50 |
| 5.3 | 100 |
| 5.2 | 55 |
| 4.3 | 75 |
| 4.1 | 50 |
| 4.0 | 45 |
| 3.8 | 60 |
| 3.5 | 55 |

Included within the scope of the present invention are the pseudomorphs and polymorphs of the hydrated and anhydrous free base of 4-[4-[4-(Hydroxydiphenylmethyl)-1-piperidinyl]-1-hydroxybutyl]-α,α-dimethylbenzeneacetic acid. The free base of 4-[4-[4-(Hydroxydiphenylmethyl)-1-piperidinyl]-1-hydroxybutyl]-α,α-dimethylbenzeneacetic acid is readily prepared utilizing techniques and procedures well known to one of ordinary skill in the art. For example, the hydrochloride salt of 4-[4-[4-(Hydroxydiphenylmethyl)-1-piperidinyl]-1-hydroxybutyl]-α,α-dimethylbenzeneacetic acid is dissolved in methanol and treated with one equivalent of aqueous sodium bicarbonate. After stirring for approximately 5 to 30 minutes, the white solid is collected by filtration, rinsed with water and air dried to provide the dihydrate of the free base of 4-[4-[4-(Hydroxydiphenylmethyl)-1-piperidinyl]-1-hydroxybutyl]-α,α-dimethylbenzeneacetic acid.

Illustrative examples of straight or branched alkyl groups having from 1 to 4 carbon atoms referred to herein are methyl, ethyl, n-propyl, isopropyl, n-butyl, isobutyl and t-butyl. Illustrative examples of straight or branched alkyl groups having from 1 to 6 carbon atoms referred to herein are methyl, ethyl, n-propyl, isopropyl, n-butyl, isobutyl, t-butyl, n-pentyl, cyclopentyl, n-hexyl and cyclohexyl. Illustrative examples of lower alkoxy groups of from 1 to 4 carbon atoms referred to herein are methoxy, ethoxy, propoxy, n-butoxy, isobutoxy, sec-butoxy and t-butoxy. The terms "halo", "halogen" or "halide" refers to a fluorine, chlorine, bromine or iodine atom.

The term "pharmaceutically acceptable salt" refers to those salts of formulas (I), (II), (III) and (IIIa) that are not substantially toxic at the dosage administered to achieve the desired effect and do not independently possess significant pharmacological activity. The salts included within the scope of this term are pharmaceutically acceptable acid addition salts of a suitable inorganic or organic acid. Suitable inorganic acids are, for example hydrochloric, hydrobromic, sulfuric and phosphoric acids. Suitable organic acids include carboxylic acids, such as acetic, propionic, glycolic, lactic, pyruvic, malonic, succinic, fumaric, malic, tartaric, citric, cyclamic, ascorbic, maleic, hydroxymaleic, dihydroxymaleic, benzoic, phenylacetic, 4-aminobenzoic, 4-hydroxybenzoic, anthranillic, cinnamic, salicylic, 4-aminosalicyclic, 2-phenoxybenzoic, 2-acetoxybenzoic and mandelic acid, sulfonic acids, such as methanesulfonic, ethanesulfonic and β-hydroxyethanesulfonic acid. In addition, pharmaceutically acceptable salts include those salts of formulas (I), (II), (III) and (IIIa) formed with inorganic and organic bases, such as those of alkali metals, for example sodium, potassium and lithium, alkaline earth metals, for example calcium and magnesium, light metals of group IIIA, for example aluminum, organic amines, for example primary, secondary or tertiary amines, such as cyclohexylamine, ethylamine, pyridine, methylaminoethanol and piperazine. The salts are prepared by conventional means by one of ordinary skill in the art as, for example, by treating a compound of formulas (I), (II), (III) or (IIIa) with an appropriate acid or base. Such salts can exist in either a hydrated or substantially anhydrous form.

As used herein, the phrase "formulas I through IIIb" refers to formulas I, II, III, IIIa and IIIb.

As used herein, the term "azeotropic mixture" refers to a liquid mixture of two or more substances which behaves like a single substance in that the vapor produced by partial evaporation of liquid has the same composition as the liquid. The constant boiling mixture exhibits either a maximum or minimum boiling point as compared with that of other mixtures of the same substance.

As used herein, the term "azeotropic distillation" refers to a type of distillation in which a substance is added to the mixture to be separated in order to form an azeotropic mixture with one or more of the constituents of the original mixture. The azeotrope or azeotropes thus formed will have boiling points different from the boiling points of the original mixture. As used herein, the term "azeotropic distillation" also refers to co-distillation.

As used herein, the term "water-minimizing recrystallization" refers to a recrystallization wherein the ratio of anhydrous solvent to substrate hydrate is such that the percentage of water present is minimized, thereby inducing precipitation of the anhydrous form of the substrate.

As used herein, the term "aqueous recrystallization" refers to those processes wherein either 1) a solid material is dissolved in a volume of water or a water/organic solvent mixture sufficient to cause dissolution and the solid material recovered by evaporation of the solvent; 2) a solid material is treated with a minimal amount of water or a water/organic solvent mixture which is not sufficient to cause dissolution, heated to obtain dissolution and cooled to induce crystallization or 3) a solid material is dissolved in a volume of water or a water/organic solvent mixture sufficient to cause dissolution and then the solvent is partially evaporated to form a saturated solution which induces crystallization.

As used herein, the term "crystal digestion" refers to that process wherein a solid material is treated with a minimal amount of water or water/organic solvent mixture which is not sufficient to cause dissolution and either heating or stirring at ambient temperature until the desired transformation has taken place.

As used herein, the term "antisolvent" refers to a poor solvent for the substance in question which when added to a solution of the substance, causes the substance to precipitate.

As used herein, the term "suitable temperature" refers to that temperature which is sufficient to cause dissolution and to permit the precipitation of the desired substance either upon addition of an antisolvent or upon removal of the co-solvent by azeotropic distillation.

The term "micronization" refers to the process of increasing the particle surface area of the piperidinoalkanol compounds or their pharmaceutically acceptable salts to greater than about 1.0 $m^2/g$.

The piperidinoalkanol compounds of formulas (I) through (IIIb) which are not subjected to micronization have a particle surface area of less than about 1.0 $m^2/g$.

The pharmaceutical composition of the present invention is administered orally in the form of a solid unit dosage form. Examples of solid unit dosage forms are tablets, coated tablets, powders, dragees, hard or soft gelatin capsules and the like. The preferred solid unit dosage forms of the present invention are capsules, tablets and the like. The most preferred solid unit dosage form are tablets. A unit dose is that amount of the pharmaceutical composition which is individually administered. The pharmaceutical compositions of the present invention are useful as antihistamines, antiallergy agents, bronchodilators and in the treatment of urticaria.

As used herein, the term "patient" refers to a warm-blooded animal, such as a mammal, which is in need of an antihistamine, antiallergy agent, bronchodilator or treatment of urticaria. It is understood that humans, mice and rats are included within the scope of the term "patient".

A therapeutically effective amount can be readily determined by the attending diagnostician, as one skilled in the art, by the use of known techniques and by observing results obtained under analogous circumstances. In determining the therapeutically effective amount or dose, a number of factors are considered by the attending diagnostician, including, but not limited to: the species of mammal; its size, age, and general health; the response of the individual patient; the particular compound administered; the mode of administration; the bioavailability characteristics of the preparation administered; the dose regimen selected; the use of concomitant medication; and other relevant circumstances.

A therapeutically effective amount of a piperidinoalkanol compound of formulas (I) through (IIIb) is that amount which produces the desired therapeutic response (ie., antihistaminic, antiallergic, bronchodilatory effect, or reduction or elimination of urticaria) upon oral administration according to a single or multiple dosage regimen. A therapeutically effective amount of a piperidinoalkanol compound of formulas (I) through (IIIb) may vary over a wide range from about 0.01 milligrams per kilogram (mg/kg) to about 20 (mg/kg) of body weight per dose. A pharmaceutical composition which provides from about 5 mg to about 360 mg of a piperidinoalkanol compound of formulas (I) through (IIIb) per unit dose is preferred and those which provide from about 40 mg to about 240 mg per unit dose are most preferred.

According to the present invention the piperidinoalkanol compounds of formulas (I) through (IIIb) when micronized have a particle surface area of greater than about 1.0 $m^2/g$. The preferred particle surface area when micronized is about 2 to 10 $m^2/g$, the most preferred particle surface area when micronized is about 2 to 6 $m^2/g$ and the most especially preferred particle surface area of the piperidinoalkanol compounds of formulas (I) through (IIIb) when micronized is about 2 to 4 $m^2/g$.

The piperidinoalkanol compounds of formulas (I) through (IIIb) are readily prepared by one of ordinary skill in the art, for example, utilizing the techniques and procedures described in U.S. Pat. Nos. 3,878,217, 4,254,129 and 4,285,957, International Application Number PCT/US93/02103 published Oct. 28, 1993, WO 93/21156, and International Application Number PCT/US94/05982, published Jan. 5, 1995, WO 95/00480 which are incorporated herein by reference.

The anhydrous, pharmaceutically acceptable acid addition salts of the piperidinoalkanol compounds of the formulas (III), and (IIIa) may be prepared from the corresponding hydrated, pharmaceutically acceptable acid addition salts of the piperidinoalkanol compounds of the formulas (III) and (IIIa) by subjecting the corresponding hydrated, pharmaceutically acceptable acid addition salts of the piperidinoalkanol compounds of the formulas (III) and (IIIa) to an azeotropic distillation.

For example, the appropriate hydrated, pharmaceutically acceptable acid addition salt of the piperidinoalkanol compounds of the formulas (III) and (IIIa) is first dissolved in a volume of a suitable solvent or solvent mixture which is sufficient to cause dissolution. Examples of such solvents are water, $C_1$–$C_5$ alkanols such as methanol, ethanol and the like; ketone solvents such as acetone, methyl ethyl ketone and the like; aliphatic ester solvents such as ethyl acetate, methyl acetate, methyl formate, ethyl formate, isopropyl acetate and the like and aqueous mixtures of these solvents, such as acetone/water, methyl ethyl ketone/water, water/acetone and water/acetone/ethyl acetate. An additional volume of the same solvent used to effect dissolution or second suitable anhydrous antisolvent is then added to this solution, which is then heated to a boiling point which is suitable to azeotropically remove water and other low boiling components. Suitable anhydrous antisolvents for use in the azeotropic distillation are, for example, ketone solvents such as acetone, methyl ethyl ketone and the like; aliphatic ester solvents such as ethyl acetate, methyl acetate, methyl formate, ethyl formate, isopropyl acetate and the like; $C_5$–$C_8$ aliphatic solvents such as pentane, hexane and the like; aliphatic nitriles, such as acetonitrile and mixtures of these solvents such as acetone/ethyl acetate and the like. The azeotropic mixture of water and solvent is removed by distillation until the temperature changes, indicating that the azeotropic mixture is completely removed. The reaction mixture is cooled and the corresponding anhydrous, pharmaceutically acceptable acid addition salts of the piperidinoalkanol compounds of the formulas (III) and (IIIa) is recovered from the reaction zone by, for example filtration.

In addition, the anhydrous, pharmaceutically acceptable acid addition salts of the piperidinoalkanol compounds of the formulas (III) and (IIIa) may be prepared from the corresponding hydrated, pharmaceutically acceptable acid addition salts of the piperidinoalkanol compounds of the formulas (III) and (IIIa) by subjecting the corresponding hydrated, pharmaceutically acceptable acid addition salts of the piperidinoalkanol compounds of the formulas (III) and (IIIa) to a water-minimizing recrystallization.

For example, the appropriate hydrated, pharmaceutically acceptable acid addition salt of the piperidinoalkanol compounds of the formulas (III) and (IIIa) is dissolved in a volume of a suitable anhydrous solvent or solvent mixture which is sufficient to cause dissolution and heated to reflux. Examples of such solvents are water, $C_1$–$C_5$ alkanols such as methanol, ethanol and the like; ketone solvents such as acetone, methyl ethyl ketone and the like; aliphatic ester solvents such as ethyl acetate, methyl acetate, methyl formate, ethyl formate, isopropyl acetate and the like and aqueous mixtures of these solvents, such as acetone/water, methyl ethyl ketone/water, water/acetone and water/acetone/ethyl acetate. An additional volume of the same solvent used to effect dissolution or second suitable anhydrous antisolvent is then added in a quantity sufficient to initiate precipitation of the anhydrous, pharmaceutically acceptable acid addition salt of the piperidinoalkanol compounds of the formulas (III) and (IIIa). Suitable anhydrous antisolvents are, for example, ketone solvents such as acetone, methyl ethyl ketone and the like; aliphatic ester solvents such as ethyl acetate, methyl acetate, methyl formate, ethyl formate, isopropyl acetate and the like; mixtures of ketone solvents and aliphatic ester solvents such as acetone/ethyl acetate and the like; $C_5$–$C_8$ aliphatic solvents such as pentane, hexane and the like; aliphatic nitrites, such as acetonitrile and mixtures of these solvents such as acetone/ethyl acetate and the like as well as mixtures of water and ketone solvents such as acetone/water and the like; and mixtures of water, ketone solvents and aliphatic ester solvents such as acetone/water/ethyl acetate. The reaction mixture is cooled and the corresponding anhydrous, pharmaceutically acceptable acid addition salt of the piperidinoalkanol compounds of the formulas (III) and (IIIa) is recovered from the reaction zone by, for example filtration.

Polymorphic forms of anhydrous 4-[4-[4-(Hydroxydiphenylmethyl)-1-piperidinyl]-1-hydroxybutyl]-α,α-dimethylbenzeneacetic acid hydrochloride (Forms I and III) may be prepared by a variety of methods as detailed below.

Form III to Form I

For example, anhydrous 4-[4-[4-(Hydroxydiphenylmethyl)-1-piperidinyl]-1-hydroxybutyl]-α,α-dimethylbenzeneacetic acid hydrochloride (Form I) may be prepared from anhydrous 4-[4-[4-(Hydroxydiphenylmethyl)-1-piperidinyl]-1-hydroxybutyl]-α,α-dimethylbenzeneacetic acid hydrochloride (Form III), by subjecting the anhydrous 4-[4-[4-(Hydroxydiphenylmethyl)-1-piperidinyl]-1-hydroxybutyl]-α,α-dimethylbenzeneacetic acid hydrochloride (Form III) to a crystal digestion as described above.

Form II to Form III

In addition, anhydrous 4-[4-[4-(Hydroxydiphenylmethyl)-1-piperidinyl]-1-hydroxybutyl]-α,α-dimethylbenzeneacetic acid hydrochloride (Form III) may be prepared from hydrated 4-[4-[4-(Hydroxydiphenylmethyl)-1-piperidinyl]-1-hydroxybutyl]-α,α-dimethylbenzeneacetic acid hydrochloride (Form II), by subjecting the hydrated 4-[4-[4-(Hydroxydiphenylmethyl)-1-piperidinyl]-1-hydroxybutyl]-α,α-dimethylbenzeneacetic acid hydrochloride (Form II) to water-minimizing recrystallization as described above.

Form II to Form I

In addition, anhydrous 4-[4-[4-(Hydroxydiphenylmethyl)-1-piperidinyl]-1-hydroxybutyl]-α,α-dimethylbenzeneacetic acid hydrochloride (Form I) may be prepared from hydrated 4-[4-[4-(Hydroxydiphenylmethyl)-1-piperidinyl]-1-hydroxybutyl]-α,α-dimethylbenzeneacetic acid hydrochloride (Form II), by subjecting the hydrated 4-[4-[4-(Hydroxydiphenylmethyl)-1-piperidinyl]-1-hydroxybutyl]-α,α-dimethylbenzeneacetic acid hydrochloride (Form II) to water-minimizing recrystallization as described above or by subjecting the hydrated 4-[4-[4-(Hydroxydiphenylmethyl)-1piperidinyl]-1-hydroxybutyl]-α,α-dimethylbenzeneacetic acid hydrochloride (Form II) to an azeotropic distillation.

Form IV to Form I

In addition, anhydrous 4-[4-[4-(Hydroxydiphenylmethyl)-1-piperidinyl]-1-hydroxybutyl]-α,α-dimethylbenzeneacetic acid hydrochloride (Form I) may be prepared from hydrated 4-[4-[4-(Hydroxydiphenylmethyl)-1-piperidinyl]-1-hydroxybutyl]-α,α-dimethylbenzeneacetic acid hydrochloride (Form IV), by subjecting the hydrated 4-[4-[4-(Hydroxydiphenylmethyl)-1-piperidinyl]-1-hydroxybutyl]-α,α-dimethylbenzeneacetic acid hydrochloride (Form IV) to water-minimizing recrystallization or to an azeotropic distillation as described above.

The hydrated, pharmaceutically acceptable acid addition salts of the piperidinoalkanol compounds of the formulas (III) and (IIIa) may be prepared from the corresponding compound of the formula (IV)

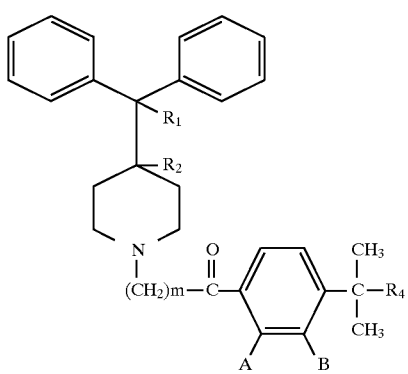

formula (IV)

wherein $R_1$ represents hydrogen or hydroxy; $R_2$ represents hydrogen; or $R_1$ and $R_2$ taken together form a second bond between the carbon atoms bearing $R_1$ and $R_2$; m is an integer of from 1 to 5; $R_4$ is —$CO_2$alkyl wherein the alkyl moiety has from 1 to 6 carbon atoms and is straight or branched; each of A and B is hydrogen or hydroxy; with the proviso that at least one of A or B is hydrogen; by subjecting the corresponding compound of formula (IV) to a reduction using an appropriate reducing agent, such as sodium borohydride, potassium borohydride, sodium cyanoborohydride, or tetramethylammonium borohydride in a suitable solvent, such as, methanol, ethanol, isopropyl alcohol or n-butanol, aqueous mixtures thereof or basic solutions thereof, at temperatures ranging from about 0° C. to the reflux temperature of the solvent, and the reaction time varies from about ½ hour to 8 hours. After quenching and acidifying with an suitable acid, such as hydrochloric acid, the hydrated, pharmaceutically acceptable acid addition salts of the piperidinoalkanol compounds of the formulas (III) and (IIIa) are recovered from the reaction zone by crystallization and filtration.

In addition, the hydrated, pharmaceutically acceptable acid addition salts of the piperidinoalkanol compounds of the formulas (III) and (IIIa) may be prepared from the corresponding anhydrous, pharmaceutically acceptable acid addition salts of the formulas (III), (IIIa) and (IIIb) by subjecting the corresponding anhydrous, pharmaceutically acceptable acid addition salts of formulas (III) and (IIIa) to an aqueous recrystallization.

For example, the appropriate anhydrous, pharmaceutically acceptable acid addition salt of the piperidinoalkanol compounds of the formula (I) and (II) is treated with a minimal volume of water or suitable water/organic solvent mixture which is insufficient to cause dissolution and heated to reflux. The reaction mixture is cooled and the corresponding hydrated, pharmaceutically acceptable acid addition salt of the piperidinoalkanol compounds of the formulas (III) and (IIIa) is recovered from the reaction zone by, for example filtration. Alternatively, the appropriate anhydrous, pharmaceutically acceptable acid addition salt of the piperidinoalkanol compounds of the formulas (III) and (IIIa) is treated with a volume of water or a suitable water/organic solvent mixture which is sufficient to cause dissolution and the water or water/organic solvent is partially or completely evaporated to a volume which induces crystallization of the hydrated, pharmaceutically acceptable acid addition salts of the piperidinoalkanol compounds of the formulas (III) and (IIIa). Suitable solvents for use in the above recrystallization are water, acetone/water, ethanol/water, methyl ethyl ketone/aqueous methanol, methyl ethyl ketone/water and the like.

The pseudomorphic forms of hydrated 4-[4-[4-(Hydroxydiphenylmethyl)-1-piperidinyl]-1-hydroxybutyl]-α,α-dimethylbenzeneacetic acid hydrochloride (Forms II and IV) may be prepared by a variety of methods as detailed below.

Ethyl Ester/Ketone to Form II

Hydrated 4-[4-[4-(Hydroxydiphenylmethyl)-1-piperidinyl]-1-hydroxybutyl]-α,α-dimethylbenzeneacetic acid hydrochloride (Form IV) may be prepared from ethyl 4-[4-[4-(hydroxydiphenylmethyl)-1-piperidinyl]-1-oxobutyl]-α,α-dimethylbenzeneacetate, hydrochloride or free base as described above for the general preparation of the hydrated, pharmaceutically acceptable acid addition salts of the piperidinoalkanol compounds of the formula (III) from the corresponding compound of the formula (IV) wherein $R_3$ is —COOalkyl, and rapidly adding water over a period of time ranging from 1 minute to 45 minutes at a temperature range of about −20° C. to 50° C. to precipitate the hydrated 4-[4-[4-(Hydroxydiphenylmethyl)-1-piperidinyl]-1-hydroxybutyl]-α,α-dimethylbenzeneacetic acid hydrochloride (Form II).

Ethyl Ester/Ketone to Form IV

Hydrated 4-[4-[4-(Hydroxydiphenylmethyl)-1-piperidinyl]-1-hydroxybutyl]-α,α-dimethylbenzeneacetic acid hydrochloride (Form IV) may be prepared from ethyl 4-[4-[4-(hydroxydiphenylmethyl)-1-piperidinyl]-1-oxobutyl]-α,α-dimethylbenzeneacetate, hydrochloride or free base as described above for the general preparation of the hydrated, pharmaceutically acceptable acid addition salts of the piperidinoalkanol compounds of the formula (III) from the corresponding compound of the formula (IV) wherein $R_3$ is —COOalkyl, slowly adding water over a period of time ranging from about 30 minutes to 24 hours and at a temperature range of about 0° C. to 50° C., optionally with seeding, to precipitate the hydrated 4-[4-[4-(Hydroxydiphenylmethyl)- 1-piperidinyl]-1-hydroxybutyl]-α,α-dimethylbenzeneacetic acid hydrochloride (Form IV).

Form I to Form II

Hydrated 4-[4-[4-(Hydroxydiphenylmethyl)-1-piperidinyl]-1-hydroxybutyl]-α,α-dimethylbenzeneacetic acid hydrochloride (Form II) may be prepared from anhydrous 4-[4-[4-(Hydroxydiphenylmethyl)-1-piperidinyl]-1-hydroxybutyl]-α,α-dimethylbenzeneacetic acid hydrochloride (Form I) by subjecting hydrated 4-[4-[4-(Hydroxydiphenylmethyl)-1-piperidinyl]-1-hydroxybutyl]-α,α-dimethylbenzeneacetic acid hydrochloride (Form II) to an aqueous recrystallization as defined above.

Starting materials for use in the present invention are readily available to one of ordinary skill in the art. For example, ethyl 4-[4-[4-(Hydroxydiphenylmethyl)-1-piperidinyl]-1-oxobutyl]-α,α-dimethylbenzeneacetate, hydrochloride is described in U.S. Pat. No. 4,254,129, Mar. 3, 1981.

Preparation of the piperidinoalkanol compounds of formulas (I) through (IIIb) with the desired particle surface area is readily performed by one of ordinary skill in the art. For example, the particle surface area can be increased by milling the piperidinoalkanol compounds with a Jet Mill (Jet-O-Mizer®, Fluid Energy Processing and Equipment Company, Hatfield, Pa.). Similar mills, such as the Micro-Jet (Fluid Energy Processing and Equipment Company) and the Sturtevant Micronizer (Sturtevant, Boston, Mass.) may also be used. With the Jet Mill, the piperidinoalkanol compound particles are accelerated in a milling chamber using compressed air. Piperidinoalkanol compound particle surface area is increased by particle-to-particle impact. The mill is designed such that the particles exit the milling chamber and are collected in a collection vessel. Fine particles are also collected in a filter bag. The particle surface area of the milled piperidinoalkanol compound is influenced by the pressure of the compressed air and by the feed of the piperidinoalkanol compound into the mill. Increased particle surface area may also be achieved by controlled crystallization of the piperidinoalkanol compound under conditions determined by one of ordinary skill in the art.

The particle surface area of the piperidinoalkanol compounds of formulas (I) through (IIIb) can be readily determined by one of ordinary skill in the art. For example, the surface area can be determined by the BET method (see S. Brunauer, P. H. Emmet and E. Teller, *J. Amer. Chem. Soc.*, 60 (1938) 309–319). A gas adsorption instrument, such as the Quantasorb® Gas Sorption System (Quantachrome Corp., Syosset, N.Y. 11791) can be used to perform a multi-point analysis using nitrogen adsorption.

As used herein the term "inert ingredient" refers to those therapeutically inert ingredients that are well known in the art of pharmaceutical science which can be used singly or in various combinations, and include, for example, binders, diluents, lubricants, glidants, sweetening agents, disintegrants, coloring agents, flavoring agents, antioxidants, solubilizing agents, coating agents and the like, as are disclosed in The United States Pharmacopeia, XXII, 1990, (1989 The United States Pharmacopeial Convention, Inc.), pages 1857–1859, which is incorporated herein by reference. For example, the following inert ingredients can be utilized singly or in various combinations; binders such as gelatin, polyvinylpyrrolidone (PVP), pregelatinized starch, povidone, cellulose derivatives including methyl cellulose, carboxymethyl cellulose, hydroxypropyl methylcellulose (HPMC), hydroxypropyl cellulose (HPC), sucrose and the like; diluents such as calcium carbonate, lactose, starch, microcrystalline cellulose, and the like; lubricants such as magnesium stearate, calcium stearate, zinc stearate, stearic acid, talc, hydrogenated vegetable oil and the like; glidants such as silicon dioxide, talc and the like; disintegrants such as alginic acid, methacrylic acid DVB, cross-linked PVP, microcrystalline cellulose, croscarmellose sodium, crospovidone, polacrilin potassium, sodium starch glycolate, starch, pregelatinized starch and the like; preferred disintegrants are croscarmellose sodium, starch, pregelatinized starch and sodium starch glycolate with croscarmellose sodium being the most preferred disintegrant; sweetening agents; coloring agents; flavoring agents; antioxidants; and the like. The above inert ingredients can be present in amounts up to about 95% of the total composition weight.

A suitable combination of inert ingredients comprises microcrystalline cellulose, pregelatinized starch, gelatin, magnesium stearate, calcium carbonate arid sodium starch glycolate, in amounts of from about 20% to about 85%, 5% to about 50%, 1% to about 15%, 0.05% to about 3%, 5% to about 50%, and 1% to about 15%. A preferred combination of inert ingredients is microcrystalline cellulose, pregelatinized starch, calcium carbonate, magnesium stearate and sodium starch glycolate in amounts of from about 20% to about 85%, 5% to about 50%, 5% to about 50%, 0.05% to about 3%, and 1% to about 15%. Another preferred combination of inert ingredients comprises: microcrystalline cellulose, pregelatinzed starch, magnesium stearate, and croscarmellose sodium in amounts of from about, 20% to about 85%, 5% to about 50%, 0.05 to about 3%, 1% to about 10%. The most preferred combination of inert ingredients is croscarmellose sodium, microcrystalline cellulose, lactose, pregelatinized starch and gelatin, in amounts of from about 1% to about 10%, 20% to about 85%, 20% to about 85%, 1% to about 30% and 1% to about 15% respectively. The most especially preferred combination of inert ingredients is croscarmellose sodium, microcrystalline cellulose, lactose, pregelatinized starch, gelatin and magnesium stearate, in amounts of from about 1% to about 10%, 20% to about 85%, 20% to about 85%, 1% to about 30%, 1% to about 15% and 0.05% to about 3% respectively. The following entries 1 through 7 in Table 5, provide the most preferred amounts of the respective inert ingredients which can be utilized in preparation of the tablet or capsule dosage forms.

TABLE 5

Preferred Amounts of Inert Ingredients

| Preferred Combination | #1 (%) | #2 (%) | #3 (%) | #4 (%) | #5 (%) | #6 (%) | #7 (%) |
|---|---|---|---|---|---|---|---|
| Croscarmellose Sodium | 4.8 | 4.8 (4.6) | — | — | 4.8 | 6 | — |
| Microcrystalline Cellulose | 33.8 | 33.7 (32.4) | 34.9 (33.5) | 36.5 (35.1) | 25.7 | 33.3 | 21.1 |
| Lactose | 33.8 | 33.7 (32.4) | — | — | 25.7 | — | — |
| Pregelatinized Starch | 9.6 | 9.6 (9.2) | 29.4 (28.3) | 31.0 (29.8) | 9.6 | 30 | 30 |
| Gelatin | 3.5 | 3.5 (3.4) | 3.3 (3.1) | — | 3.5 | — | — |
| Magnesium Stearate | — | 0.5 (0.5) | 0.5 (0.5) | 0.5 (0.5) | 0.75 | 0.75 | 0.75 |
| Calcium Carbonate | — | — | 15.6 (15.0) | 15.6 (15.0) | — | — | 15.6 |
| Sodium Starch Glycolate | — | — | 5.6 (5.4) | 5.6 (5.4) | — | — | 10.0 |

The above entries in Table 5 represent percent by weight of the composition. The entries in parentheses for entries #2, #3, and #4 represent the percent by weight of the composition after coating the tablet. It is understood by one of ordinary skill in the art that the above combinations of inert ingredients, when combined with the chosen piperidinoalkanol compound of formulas (I) through (IIIb), such as 4-[4-[4-(hydroxydiphenylmethyl)-1-piperidinyl]-1-hydroxybutyl]-α,α-dimethylbenzeneacetic acid hydrochloride or polymorphs, pseudomorphs or mixtures thereof, are then manufactured in the chosen solid unit dosage form, such as a capsule or tablet, utilizing techniques well known in the art of pharmaceutical science.

In general, solid unit dosage forms of the present invention can be formulated and manufactured in capsule form using the following procedure:

The desired inert ingredients are blended together with the piperidinoalkanol compound of formulas (I) through (IIIb) utilizing techniques and procedures well known to one of ordinary skill in the art. For example, microcrystalline cellulose, lactose, pregelatinized starch and a piperidinoalkanol compound of formulas (I) through (IIIb), such as 4-[4-[4-(hydroxydiphenylmethyl)-1-piperidinyl]-1-hydroxybutyl]-α,α-dimethylbenzeneacetic acid hydrochloride with a particle surface area of greater than about 1 m$^2$/g, are blended together. A solution of gelatin in water is added and mixed in with the powder blend. The resulting wet granulation is then dried and milled to uniform size. Croscarmellose sodium is then added to the milled granulation and blended to produce the final granulation. This granulation is then filled into hard gelatin capsules under conventional conditions as is well known to one of ordinary skill in the art.

In general, solid unit dosage forms of the present invention can be formulated and manufactured in tablet form using one of the following procedures:

The desired inert ingredients are blended together with the piperidinoalkanol compound of formulas (I) through (IIIb) utilizing techniques and procedures well known to one of ordinary skill in the art. For example, microcrystalline cellulose, lactose, pregelatinized starch and a piperidinoalkanol compound of formulas (I) through (IIIb), such as 4-[4-[4-(hydroxydiphenylmethyl)-1-piperidinyl]-1-hydroxybutyl]-α,α-dimethylbenzeneacetic acid hydrochloride or polymorphs, pseudomorphs or mixtures thereof, with a particle surface area of greater than about 1.0 m²/g, are blended together. A solution of gelatin in water is added and mixed in with the powder blend. The resulting wet granulation is then dried and milled to uniform size. Croscarmellose sodium and magnesium stearate are then added to the milled granulation and blended to produce the final granulation. This granulation is then compressed into tablets under conventional conditions as is well known to one of ordinary skill in the art. The compressed tablets can be film coated using standard ingredients and procedures commonly used and well known in the art of pharmaceutical science.

In an additional general procedure, microcrystalline cellulose, the pregelatinized starch, part of the croscarmellose sodium and a piperidinoalkanol compounds of formulas (I) through (IIIb), such as 4-[4-[4-(hydroxydiphenylmethyl)-1-piperidinyl]-1-hydroxybutyl]-α,α-dimethylbenzeneacetic acid hydrochloride are blended together. Water is added and mixed with the powder blend. The resulting wet granulation is then dried and milled to a uniform size. Additional microcrystalline cellulose and croscarmellose sodium are added to the granulation and blended. Finally, magnesium stearate is added and blended with the mixture to produce the final granulation. This granulation is then compressed into tablets under conventional conditions well known to one of ordinary skill in the art. The compressed tablets can be film coated using standard ingredients and procedures used and well known in the art of pharmaceutical science.

Another example would include blending microcrystalline cellulose, the pregelatinized starch, the calcium carbonate, part of the sodium starch glycolate, and a compound of formulas (I) through (IIIb), such as 4-[4-[4-(hydroxydiphenylmethyl)-1-piperidinyl]-1-hydroxybutyl]-α,α-dimethylbenzeneacetic acid hydrochloride or polymorphs, pseudomorphs or mixtures thereof. Water is added and mixed with the powder blend. The resulting wet granulation is then dried and milled to a uniform size. Additional microcrystalline cellulose and the remaining sodium starch glycolate are blended together. The resulting mixture is blended with the magnesium stearate to produce the final granulation. This granulation is then compressed into tablets under conventional conditions well known to one of ordinary skill in the art. The compressed tablets can be filmed coated using standard ingredients and procedures used and well known in the art of pharmaceutical science.

The above procedures may also be used for preparation of solid unit dosage forms wherein the piperidinoalkanol compound of formulas (I) through (IIIb), such as 4-[4-[4-(hydroxydiphenylmethyl)-1-piperidinyl]-1-hydroxybutyl]-α,α-dimethylbenzeneacetic acid hydrochloride or polymorphs, pseudomorphs or mixtures thereof, has a particle surface area less than about 1 m²/g.

For the entries 1 through 4 in Table 5, wherein the solid unit dosage form is a tablet, the quantity of compound of the formula;

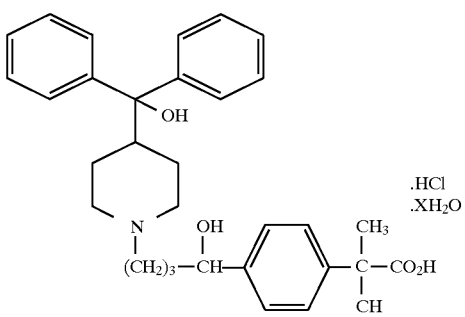

herein X is a number ranging from about zero to 5, and the individual optical isomers thereof, dissolved in 45 minutes, is not less than 75% of label in water, at a temperature of about 37° C. and about 50 rpm when measured according to USP Apparatus 2 as is disclosed in the United States Pharmacopeia, 23, U.S. Pharmacopeial Convention, Inc., Rockville, Md., 20852 (1995), pages 1791–1793 which is hereby incorporated by reference.

For the entries 5 through 7 in Table 5, wherein the solid unit dosage form is a tablet, the quantity of compound of the formula;

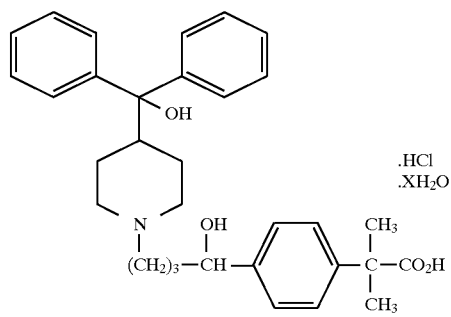

wherein X is a number ranging from about zero to 5, and the individual optical isomers thereof, dissolved in 45 minutes, is not less than 75% of label in 0.001N aqueous hydrochloric acid, at a temperature of about 37° C. and about 50 rpm when measured according to USP Apparatus 2 as is disclosed in the United States Pharmacopeia, 23, U.S. Pharmacopeial Convention, Inc., Rockville, Md., 20852 (1995), pages 1791–1793, which is hereby incorporated by reference.

The following examples are understood to be illustrative only and are not intended to limit the scope of the present invention in any way. The reagents and starting materials are available to one of ordinary skill in the art. As used herein, the following terms have the indicated meanings: "m²/g" refers to square meters per gram and is used as a measurement of particle surface area; "kg" refers to kilograms; "g" refers to grams; "mmol" refers to millimoles; "ml" refers to milliliters; "bp" refers to boiling point; "mp" refers to melting point; "°C." refers to degrees Celsius; "°F." refers to degrees Fahrenheit; "mm Hg" refers to millimeters of mercury; "µL" refers to micro-liters; and "µg" refers to micrograms.

EXAMPLE 1

20 mg Gelatin Capsules for Oral Administration

Combine 32.4 kg of 4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$, 76.1 kg microcrystalline cellulose, 76.1 kg lactose, and 21.6 kg pregelatinized starch and blend in a mixer for 5 minutes. To this mixture, add a solution of 7.9 kg of gelatin in 55.0 kg purified water (prepared by adding the gelatin to the water and heating the dispersion with mixing until solution of the gelatin is attained) and continue mixing until a good granulation is formed. Pass the granulation through a 0.375 inch screen and dry at 60° C. until a moisture content of less than 3.0% is achieved as determined by a Computrac moisture balance at 125° C. Mill the dried granulation through a 0.065 inch screen. To the granulation add 10.8 kg of croscarmellose sodium and mix for about 10 minutes. Fill the granulation into size 3 hard gelatin capsules to a fill weight of 138.9 mg granulation per capsule. This procedure results in about 1,620,000 capsules of the composition shown in table 6 below.

TABLE 6

Composition of 20 mg Gelatin Capsules.

| INGREDIENT | AMOUNT mg/capsule | COMPOSITION % by weight |
|---|---|---|
| Piperidinoalkanol Compound* | 20.0 | 14.4 |
| Microcrystalline Cellulose | 47.0 | 33.8 |
| Lactose | 47.0 | 33.8 |
| Pregelatinized Starch | 13.3 | 9.6 |
| Croscarmellose Sodium | 6.7 | 4.8 |
| Gelatin | 4.9 | 3.5 |

*4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$.

EXAMPLE 2

30 mg Capsules for Oral Administration

Combine 144.0 g of 4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$, 338.5 g microcrystalline cellulose, 338.5 g lactose, and 96.0 g pregelatinized starch in a blender and blend. To the powder blend, add a solution of 35.0 g of gelatin in 286.1 g of purified water (prepared by adding the gelatin to the water and heating the dispersion with mixing until solution of the gelatin is attained) and continue mixing until a good granulation is formed. Pass the granulation through a screen, if necessary, and dry the granulation. Mill the dried granulation. To the milled granulation in a blender, add 48.0 g of croscarmellose sodium and blend. Fill the finished granulation into size 1 hard gelatin capsules to the desired weight. This procedure results in 4801 capsules each with a total fill weight of 208.3 mg with the composition shown in table 7 below.

TABLE 7

Composition of 30 mg Capsules.

| INGREDIENT | AMOUNT mg/capsule | COMPOSITION % by weight |
|---|---|---|
| Piperidinoalkanol Compound* | 30.0 | 14.4 |
| Microcrystalline Cellulose | 70.5 | 33.8 |
| Lactose | 70.5 | 33.8 |
| Pregelatinized Starch | 20.0 | 9.6 |
| Gelatin | 7.3 | 3.5 |
| Croscarmellose Sodium | 10.0 | 4.8 |

*4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$.

EXAMPLE 3

30 mg Capsules for Oral Administration

Combine 144.1 g of 4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$, 338.5 g microcrystalline cellulose, 338.5 g lactose, and 96.0 g pregelatinized starch in a blender and blend. To the powder blend, add a solution of 35.1 g of gelatin in 286.2 g of purified water (prepared by adding the gelatin to the water and heating the dispersion with mixing until solution of the gelatin is attained) and continue mixing until a good granulation is formed. Pass the granulation through a screen, if necessary, and dry the granulation. Mill the dried granulation. To the milled granulation in a blender, add 48.0 g of croscarmellose sodium and blend. Add 4.8 g of magnesium stearate to the blend and blend further. Fill the finished granulation into size 1 hard gelatin capsules to the desired weight. This procedure results in 4802 capsules each with a total fill weight of 209.3 mg with the composition shown in table 8 below.

TABLE 8

Composition of 30 mg Capsules.

| INGREDIENT | AMOUNT mg/capsule | COMPOSITION % by weight |
|---|---|---|
| Piperidinoalkanol Compound* | 30.0 | 14.3 |
| Microcrystalline Cellulose | 70.5 | 33.7 |
| Lactose | 70.5 | 33.7 |
| Pregelatinized Starch | 20.0 | 9.6 |
| Gelatin | 7.3 | 3.5 |
| Croscarmellose Sodium | 10.0 | 4.8 |
| Magnesium Stearate | 1.0 | 0.5 |

*4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$.

EXAMPLE 4

40 mg Gelatin Capsules for Oral Administration

Combine 32.4 kg of 4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$, 76.1 kg microcrystalline cellulose, 76.1 kg lactose, and 21.6 kg pregelatinized starch and blend in a mixer for 5 minutes. To this mixture, add a solution of 7.9 kg of gelatin in 55.0 kg purified water (prepared by adding the gelatin to the water and heating the dispersion with mixing until solution of the gelatin is attained) and continue mixing until a good granulation is formed. Pass the granulation through a 0.375 inch screen and dry at 60° C. until a moisture content of less than 3.0% is achieved as determined by a Computrac moisture balance at 125° C. Mill the dried granulation through a 0.065 inch screen. To the granulation add 10.8 kg of croscarmellose sodium and mix for about 10 minutes. Fill the granulation into size 1 hard gelatin capsules to a total fill weight of 277.8 mg granulation per capsule. This procedure results in about 810,000 capsules of the composition shown in table 9 below.

TABLE 9

Composition of 40 mg Gelatin Capsules.

| INGREDIENT | AMOUNT mg/capsule | COMPOSITION % by weight |
|---|---|---|
| Piperidinoalkanol Compound* | 40.0 | 14.4 |
| Microcrystalline Cellulose | 94.0 | 33.8 |
| Lactose | 94.0 | 33.8 |
| Pregelatinized Starch | 26.6 | 9.6 |
| Croscarmellose Sodium | 13.3 | 4.8 |
| Gelatin | 9.8 | 3.5 |

*4-[4-[4-(Hydroxydiphenylmethyl)-1-piperidinyl]-1-hydroxybutyl]-α,α-dimethylbenzeneacetic acid hydrochloride with a particle surface area of about 2–4 m²/g.

EXAMPLE 5

60 mg Gelatin Capsules for Oral Administration

Combine 32.4 kg of 4-[4-[4-(Hydroxydiphenylmethyl)-1-piperidinyl]-1-hydroxybutyl]-α,α-dimethylbenzeneacetic acid hydrochloride with a particle surface area of about 2–4 m²/g, 76.1 kg microcrystalline cellulose, 76.1 kg lactose, and 21.6 kg pregelatinized starch and blend in a mixer for 5 minutes. To this mixture, add a solution of 7.9 kg of gelatin in 55.0 kg purified water (prepared by adding the gelatin to the water and heating the dispersion with mixing until solution of the gelatin is attained) and continue mixing until a good granulation is formed. Pass the granulation through a 0.375 inch screen and dry at 60° C. until a moisture content of less than 3.0% is achieved as determined by a Computrac moisture balance at 125° C. Mill the dried granulation through a 0.065 inch screen. To the granulation add 10.8 kg of croscarmellose sodium and mix for about 10 minutes. Fill the granulation into size 0 hard gelatin capsules to a total fill weight of 416.7 mg granulation per capsule. This procedure results in about 540,000 capsules of the composition shown in table 10 below.

TABLE 10

Composition of 60 mg Gelatin Capsules.

| INGREDIENT | AMOUNT mg/capsule | COMPOSITION % by weight |
|---|---|---|
| Piperidinoalkanol Compound* | 60.0 | 14.4 |
| Microcrystalline Cellulose | 141.0 | 33.8 |
| Lactose | 141.0 | 33.8 |
| Pregelatinized Starch | 40.0 | 9.6 |
| Croscarmellose Sodium | 20.0 | 4.8 |
| Gelatin | 14.7 | 3.5 |

*4-[4-[4-(Hydroxydiphenylmethyl)-1-piperidinyl]-1-hydroxybutyl]-α,α-dimethylbenzeneacetic acid hydrochloride with a particle surface area of about 2–4 m²/g.

EXAMPLE 6

30 mg Tablets for Oral Administration

Combine 144.1 g of 4-[4-[4-(Hydroxydiphenylmethyl)-1-piperidinyl]-1-hydroxybutyl]-α,α-dimethylbenzeneacetic acid hydrochloride with a particle surface area of about 2–4 m²/g, 338.5 g microcrystalline cellulose, 338.5 g lactose, and 96.0 g pregelatinized starch and blend in a mixer for 5 minutes. To the powder blend, add a solution of 35.1 g of gelatin in 286.2 g purified water (prepared by adding the gelatin to the water and heating the dispersion with mixing until solution of the gelatin is attained) and continue mixing until a good granulation is formed. Pass the granulation through a screen, if necessary and dry the granulation. Mill the dried granulation, add 48.0 g of croscarmellose sodium and mix in a blender. Then add 4.8 g of magnesium stearate to the blender and blend further. Compress the finished granulation into tablets. Place the tablets into a coating pan and coat the tablets with a dispersion of 30.3 g of Opadry YS-1-18027-A (Colorcon, West Point Pa.) in 138.0 g of water and a dispersion of 10.6 g of Opadry YS-1-19016 (Colorcon, West Point Pa.) in 121.9 g of water. This procedure results in 4802 tablets each with a total weight of 217.8 mg with the composition shown in table 11 below. The percentages in parentheses in table 11 represent the percent by weight of the composition after coating the tablet.

TABLE 11

Composition of 30 mg Gelatin Capsules.

| INGREDIENT | AMOUNT mg/capsule | COMPOSITION % by weight |
|---|---|---|
| Piperidinoalkanol Compound* | 30.0 | 14.3 (13.8) |
| Piperidinoalkanol Compound* | 30.0 | 14.3 (13.8) |
| Microcrystalline Cellulose | 70.5 | 33.7 (32.4) |
| Lactose | 70.5 | 33.7 (32.4) |
| Pregelatinized Starch | 20.0 | 9.6 (9.2) |
| Croscarmellose Sodium | 10.0 | 4.8 (4.6) |
| Gelatin | 7.3 | 3.5 (3.4) |
| Magnesium Stearate | 1.0 | 0.5 (0.5) |
| Opadry YS-1-18027-A | 6.3 | — (2.9) |
| Opadry YS-1-19016 | 2.2 | — (1.0) |

*4-[4-[4-(Hydroxydiphenylmethyl)-1-piperidinyl]-1-hydroxybutyl]-α,α-dimethylbenzeneacetic acid hydrochloride with a particle surface area of about 2–4 m²/g.

EXAMPLE 7

30 mg Tablets for Oral Administration

Combine 149.9 g of 4-[4-[4-(Hydroxydiphenylmethyl)-1-piperidinyl]-1-hydroxybutyl]-α,α-dimethylbenzeneacetic acid hydrochloride with a particle surface area of about 2–4 m²/g, 214.2 g microcrystalline cellulose, 218.7 g calcium carbonate, and 411.6 g pregelatinized starch in a blender and blend. To the powder blend, add a solution of 45.5 g of gelatin in 400.0 g of purified water (prepared by adding the gelatin to the water and heating the dispersion with mixing until solution of the gelatin is attained) and continue mixing until a good granulation is formed. Pass the granulation through a screen, if necessary, and dry the granulation. Screen the remaining microcrystalline cellulose and add the 274.1 g of microcrystalline cellulose with 78.3 g sodium starch glycolate to the dried granulation in a blender and blend. Screen the magnesium stearate and add the 7.5 g of magnesium stearate to the blend and blend further. Compress the finished granulation into tablets. Place the tablets into a coating pan and coat the tablets with a dispersion of 42.0 g of Opadry YS-1-18027-A (Colorcon, West Point Pa.) in 191.0 g of water and a dispersion of 14.5 g of Opadry YS-1-19016 (Colorcon, West Point Pa.) in 166.8 g of water. This procedure results in 4999 tablets each with a total weight of 291.3 mg with the composition shown in table 12 below. The percentages in parentheses in table 12 represent the percent by weight of the composition after coating the tablet.

TABLE 12

Composition of 30 mg Tablets.

| INGREDIENT | AMOUNT mg/capsule | COMPOSITION % by weight |
|---|---|---|
| Piperidinoalkanol Compound* | 30.0 | 10.7 (10.3) |
| Microcrystalline Cellulose | 97.7 | 34.9 (33.5) |
| Calcium Carbonate | 43.7 | 15.6 (15.0) |
| Pregelatinized Starch | 82.3 | 29.4 (28.3) |
| Gelatin | 9.1 | 3.3 (3.1) |
| Sodium Starch Glycolate | 15.7 | 5.6 (5.4) |
| Magnesium Stearate | 1.5 | 0.5 (0.5) |
| Opadry YS-1-18027-A | 8.4 | — (2.9) |
| Opadry YS-1-19016 | 2.9 | — (1.0) |

*4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$.

EXAMPLE 8

30 mg Tablets for Oral Administration

Combine 149.9 g of 4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$, 214.2 g microcrystalline cellulose, 218.7 g calcium carbonate, and 434.3 g pregelatinized starch in a blender and blend. To the powder blend, add 460.0 g of purified water and blend until a good granulation is formed. Pass the granulation through a screen, if necessary, and dry the granulation. Screen the remaining microcrystalline cellulose and add the 296.8 g of microcrystalline cellulose with 78.3 g sodium starch glycolate to the dried granulation in a blender and blend. Screen the magnesium stearate and add the 7.5 g of magnesium stearate to the blend and blend further. Compress the finished granulation into tablets. Place the tablets into a coating pan and coat the tablets with a dispersion of 42.0 g of Opadry YS-1-18027-A (Colorcon, West Point Pa.) in 191.3 g of water and a dispersion of 14.5 g of Opadry YS-1-19016 (Colorcon, West Point Pa.) in 166.8 g water. This procedure results in 4999 tablets each with a total weight of 291.3 mg with the composition shown in table 13 below. The percentages in parentheses in table 13 represent the percent by weight of the composition after coating the tablet.

TABLE 13

Composition of 30 mg Tablets.

| INGREDIENT | AMOUNT mg/capsule | COMPOSITION % by weight |
|---|---|---|
| Piperidinoalkanol Compound* | 30.0 | 10.7 (10.3) |
| Microcrystalline Cellulose | 102.2 | 36.5 (35.1) |
| Calcium Carbonate | 43.7 | 15.6 (15.0) |
| Pregelatinized Starch | 86.9 | 31.0 (29.8) |
| Sodium Starch Glycolate | 15.7 | 5.6 (54) |
| Magnesium Stearate | 1.5 | 0.5 (0.5) |
| Opadry YS-1-18027-A | 8.4 | — (2.9) |
| Opadry YS-1-19016 | 2.9 | — (1.0) |

*4-[4-[4-(Hydroxydiphenylmethyl)-1-piperidinyl]-1-hydroxybutyl]-α,α-dimethylbenzeneacetic acid hydrochloride with a particle surface area of about 2–4 $m^2/g$.

EXAMPLE 9

In a manner analogous to the procedures described in examples 1 through 8, the respective tablets and capsules can be prepared utilizing 4-[4-[4-(hydroxydiphenylmethyl)-1-piperidinyl]-1-hydroxybutyl]-α,α-dimethylbenzeneacetic acid hydrochloride with a particle surface area of about 2 $m^2/g$ to about 6 $m^2/g$.

EXAMPLE 10

In a manner analogous to the procedures described in examples 1 through 8, the respective tablets and capsules can be prepared utilizing 4-[4-[4-(hydroxydiphenylmethyl)-1-piperidinyl]-1-hydroxybutyl]-α,α-dimethylbenzeneacetic acid hydrochloride with a particle surface area of about 2 $m^2/g$ to about 10 $m^2/g$.

EXAMPLE 11

In a manner analogous to the procedures described in examples 1 through 8, the respective tablets and capsules can be prepared utilizing 4-[4-[4-(hydroxydiphenylmethyl)-1-piperidinyl]-1-hydroxybutyl]-α,α-dimethylbenzeneacetic acid hydrochloride with a particle surface area greater than about 1 $m^2/g$.

EXAMPLE 12

In a manner analogous to the procedures described in examples 1 through 8, the respective tablets and capsules can be prepared utilizing 4-[4-[4-(hydroxydiphenylmethyl)-1-piperidinyl]-1-hydroxybutyl]-α,α-dimethylbenzeneacetic acid hydrochloride which has not been subjected to micronization such that the 4-[4-[4-(Hydroxydiphenylmethyl)-1-piperidinyl]-1-hydroxybutyl]-α,α-dimethylbenzeneacetic acid hydrochloride has a particle surface area of less than about 1.0 $m^2/g$.

EXAMPLE 13

Utilizing the procedures described in examples 1 through 12, the tablets and capsules may contain 4-[4-[4-(hydroxydiphenylmethyl)-1-piperidinyl]-1-hydroxybutyl]-α,α-dimethylbenzeneacetic acid hydrochloride in amounts from about 5 mg to about 120 mg. The 4-[4-[4-(hydroxydiphenylmethyl)- 1-piperidinyl]-1-hydroxybutyl]-α,α-dimethylbenzeneacetic acid hydrochloride and inert ingredients are present in the described percentage amounts by weight, which are readily determined by one of ordinary skill in the art from the previous examples. For example, one of ordinary skill in the art, following the procedures of examples 1 through 12 in an analogous manner, can prepare tablets and capsules, in addition to those already set forth, wherein 4-[4-[4-(hydroxydiphenylmethyl)-1-piperidinyl]-1-hydroxybutyl]-α,α-dimethylbenzeneacetic acid hydrochloride is present in amounts of 10 mg, 20 mg, 30 mg, 40 mg, 50 mg, 60 mg, 70 mg, 80 mg, 90 mg, 100 mg, 110 mg and 120 mg.

EXAMPLE 14

180 mg Tablet for Oral Administration

Combine 180.0 g of 4-[4-[4-(hydroxydiphenylmethyl)-1-piperidinyl]-1-hydroxybutyl]-α,α-dimethylbenzeneacetic acid hydrochloride, 78.0 g of microcrystalline cellulose (Avicel PH101) 180.0 g of pregelatinized starch, and part of the 36.0 g of the sodium croscarmellose in a blender and blend. To the powder blend, add 180 g of purified water and mix. Dry the resulting wet granulation. Screen the dried granulation through a 20 mesh screen. Transfer the granulation to a blender and add 121.5 g of microcrystalline cellulose (Avicel PH102) and the remaining amount of the Sodium Croscarmellose. Blend these components. Add 4.5 g of magnesium stearate and blend. Compress the finished granulation into tablets. Table 14 provides the composition of each tablet in percent by weight prior to coating the tablet.

To coat the compressed tablets with a peach aqueous coating, prepare an aqueous suspension comprised of 2.84 g of hydroxypropyl methyl cellulose (USP2910 E-15), 1.89 g of hydroxypropyl methyl cellulose (USP2910E-5) 0.51 g of Povidone (USP), 2.02 g of titanium dioxide (USP), 0.025 g of pink iron oxide blend, 0.04 g of yellow iron oxide blend, 0.73 g of silicone dioxide (M7) 3.94 g of polyethylene glycol 400 (N.F.), and about 88 g of purified water. Place the tablets into a coating pan and coat the tablets using the peach aqueous suspension to achieve about a 3% weight gain. This procedure provides a tablet with a total weight of 618.0 mg.

TABLE 14

Composition of 180 mg Tablets.

| INGREDIENT | Amount mg/tablet | Composition % Weight |
|---|---|---|
| Piperidinoalkanol Compound* | 180.0 | 30.0 |
| Microcrystalline Cellulose | 199.5 | 33.3 |
| Pregelatinized Starch | 180.0 | 30.0 |
| Croscarmellose Sodium | 36.0 | 6.0 |
| Magnesium Stearate | 4.5 | 0.75 |

*4-[4-[4-(hydroxydiphenylmethyl)-1-piperidinyl)-1-hydroxybutyl]-α,α-dimethylbenzeneacetic acid hydrochloride with a particle surface area of about 2–4 m$^2$/g.

EXAMPLE 15

180 mg Tablet for Oral Administration

Combine 180.0 g of 4-[4-[4-(hydroxydiphenylmethyl)-1-piperidinyl]-1-hydroxybutyl]-α,α-dimethylbenzeneacetic acid hydrochloride, 84.5 g of microcrystalline cellulose (Avicel PH101), 240 g of pregelatinzed starch, 125.0 g of calcium carbonate (Heavy), and part of the 80.0 g of the Sodium starch glycolate in a blender and blend. To the powder mix, add 224 g of water and mix. Dry the resulting wet granulation. Screen the dried granulation through a 20 mesh screen. Transfer the granulation to a blender. Add 84.5 g of microcrystalline cellulose (Avicel PH102) and the remaining amount of the sodium starch glycolate. Blend these components. Add 6.0 g of magnesium stearate and blend. Compress the finished granulation into Tablets. Table 15 provides the composition of each tablet in percent by weight prior to coating the tablet.

To coat the compressed tablets with a white aqueous coating, prepare an aqueous suspension comprised of 2.84 g of hydroxypropyl methyl cellulose (USP2910 E-15), 1.89 g of hydroxypropyl methyl cellulose (USP2910E-5) 0.51 g of Povidone (USP), 2.1 g of titanium dioxide (USP), 0.73 g of silicone dioxide (M7) 3.94 g of polyethylene glycol 400 (N.F.), and about 88 g of purified water. Place the tablets into a coating pan and coat the tablets using the white aqueous suspension to achieve about a 3% weight gain. This procedure provides a tablet with a total weight of 824.0 mg.

TABLE 15

Composition of 180 mg Tablets.

| INGREDIENT | Amount mg/tablet | Composition % Weight |
|---|---|---|
| Piperidinoalkanol Compound* | 180.0 mg | 22.5 |
| Microcrystalline Cellulose | 169.0 | 21.1 |
| Pregelatinized Starch | 240.0 | 30.0 |
| Sodium Starch glycolate | 80.0 | 10.0 |
| Calcium Carbonate | 125.0 | 15.6 |
| Magnesium Stearate Special | 6.0 | 0.75 |

*4-[4-[4-(hydroxydiphenylmethyl)-1-piperidinyl)-1-hydroxybutyl]-α,α-dimethylbenzeneacetic acid hydrochloride with a particle surface area of about 2–4 m$^2$/g.

EXAMPLE 16

180 mg Tablet for Oral Administration

Combine 180.0 g of 4-[4-[4-(hydroxydiphenylmethyl)-1-piperidinyl]-1-hydroxybutyl]-α,α-dimethylbenzeneacetic acid hydrochloride, 154.0 g of microcrystalline cellulose (Avicel PH101), 57.5 g of pregelatinized starch, and 154 g of lactose (hydrous, Fast-Flo) in a blender and blend. Prepare a granulating liquid by adding 21.2 g of gelatin to 142 g of water and heating the dispersion.

Add the granulating liquid to the powder blend and mix. Dry the resulting wet granulation. Screen the dried granulation through a 20 mesh screen. Transfer the granulation to a blender. Add 28.8 g of Sodium Croscarmellose to the granulation and blend. Add 4.5 g of magnesium stearate to the granulation and blend. Compress the finished granulation into tablets. Table 16 provides the composition of each tablet in percent by weight prior to coating the tablet.

The finished tablets may be coated in a manner analogous to those described in example 14 with the peach aqueous coating or in example 15 with the white aqueous coating.

TABLE 16

Composition of 180 mg Tablets.

| INGREDIENT | Amount mg/tablet | Composition % Weight |
|---|---|---|
| Piperidinoalkanol Compound* | 180.0 | 30.0 |
| Microcrystalline Cellulose | 154 | 25.7 |
| pregelatinzed starch | 57.5 | 9.6 |
| Lactose | 154.0 | 25.7 |
| Gelatin | 21.2 | 3.5 |
| Sodium Croscarmellose | 28.8 | 4.8 |
| Magnesium Stearate | 4.5 | 0.75 |

*4-[4-[4-(hydroxydiphenylmethyl)-1-piperidinyl]-1-hydroxybutyl]-α,α-dimethylbenzeneacetic acid hydrochloride with a particle surface area of about 2–4, m$^2$/g.

EXAMPLE 17

60 mg Tablets for Oral Administration

Combine 60 g of 4-[4-[4-(Hydroxydiphenylmethyl)-1-piperidinyl]-1-hydroxybutyl]-α,α-dimethylbenzeneacetic acid hydrochloride 141.0 g of microcrystalline cellulose, 141.0 g lactose, and 40 g pregelatinized starch and blend in a mixer. To this mixture, add a solution of 14.7 g of gelatin in 101.9 g purified water (prepared by adding the gelatin to the water and heating the dispersion with mixing until solution of the gelatin is attained) and continue mixing until a granulation is formed. Pass the granulation through a screen and dry. To the granulation add 20.0 g of croscarmellose sodium and mix. Then add 2.1 g of magnesium stearate to the blend and blend further. Compress the finished granulation into tablets. Table 17 provides the composition of each tablet in percent by weight prior to coating the tablet.

The resulting tablets may be coated in a manner analogous to that described in example 6 with Opadry YS-1-18027-A and Opadry YS-1-19016. Alternatively, the resulting tablets may be coated in a manner analogous to that described in example 14 with the peach aqueous coating or in example 15 with the white aqueous coating.

TABLE 17

Composition of 60 mg Tablets.

| INGREDIENT | Amount mg/tablet | Composition % Weight |
|---|---|---|
| Piperidinoalkanol Compound* | 60.0 | 14.3 |
| Microcrystalline Cellulose | 141.0 | 33.7 |
| Lactose | 141.0 | 33.7 |
| Pregelatinized Starch | 40.0 | 9.6 |
| Sodium Croscarmellose | 20.0 | 4.8 |
| Gelatin | 14.7 | 3.5 |
| Magnesium Stearate | 2.1 | 0.5 |

*4-[4-[4-Hydroxydiphenylmethyl)-1-piperidinyl]-1-hydroxybuyl]-α,α-dimethylbenzeneacetic acid hydrochloride with a particle surface area of about 2–4 m²/g.

EXAMPLE 18

In a manner analogous to the procedures described in examples 14 through 17, the tablets can be prepared utilizing 4-[4-[4-(hydroxydiphenylmethyl)-1-piperidinyl]-1-hydroxybutyl]-α,α-dimethylbenzeneacetic acid hydrochloride with a particle surface area of about 2 m²/g to about 6 m²/g.

EXAMPLE 19

In a manner analogous to the procedures described in examples 14 through 17, the tablets can be prepared utilizing 4-[4-[4-(hydroxydiphenylmethyl)-1-piperidinyl]-1-hydroxybutyl]-α,α-dimethylbenzeneacetic acid hydrochloride with a particle surface area of about 2 m²/g to about 10 m²/g.

EXAMPLE 20

In a manner analogous to the procedures described in examples 14 through 17, the tablets can be prepared utilizing 4-[4-[4-(hydroxydiphenylmethyl)-1-piperidinyl]-1-hydroxybutyl]-α,α-dimethylbenzeneacetic acid hydrochloride with a particle surface area greater than about 1 m²/g.

EXAMPLE 21

In a manner analogous to the procedures described in examples 14 through 17, the respective tablets and capsules can be prepared utilizing 4-[4-[4-(hydroxydiphenylmethyl)-1-piperidinyl]-1-hydroxybutyl]-α,α-dimethylbenzeneacetic acid hydrochloride which has not been subjected to micronization such that the 4-[4-[4-(Hydroxydiphenylmethyl)-1-piperidinyl]-1--hydroxybutyl]-α,α-dimethylbenzeneacetic acid hydrochloride has a particle surface area of less than about 1.0 m²/g.

The following examples present typical processes for preparing the anhydrous and hydrated, pharmaceutically acceptable acid addition salts of the piperidinoalkanol compounds of the formulas (III) and (IIIa), polymorphs and pseudomorphs thereof. These examples are understood to be illustrative only and are not intended to limit the scope of the present invention in any way.

Differential Scanning Calorimetry analysis were performed using a TA 2910 DSC with open aluminum pans. The samples were heated to 240° C. at 5° C./minute with a 50 mL/minute nitrogen purge.

X-Ray Powder Diffraction analyses were performed as follows:

The samples were loaded into a quartz (zero scatter) sample holder for the XRPD pattern measurement. The XRPD patterns were measured using a powder diffractometer equipped with a Co X-ray tube source, primary beam monochromator, and position sensitive detector (PSD). The incident beam was collimated using a 1° divergence slit. The active area on the PSD subtended approximately 5°2θ. The source was operated at 35 kV and 30 mA and the sample was illuminated with Co Kα$_1$ radiation. XRPD data were collected from 5° to 55° 2θ at a rate of 0.25°2θ, minute and a step width of 0.02°2θ. The XRPD patterns were measured without the addition of an internal calibrant.

Peak positions and intensities for the most prominent features were measured using a double-derivative peak picking method. X-ray peaks with $I/I_o$ greater than 20% were reported. The cutoff was chosen arbitrarily. The intensities are rounded to the nearest 5%. Certain peaks appear sensitive to preferred orientation that is caused by changes in crystallite morphology. This results in large changes in the $I/I_o$ value.

EXAMPLE 22

Preparation of Form II 4-[4-[4-(Hydroxydiphenylmethyl)-1-piperidinyl]-1-hydroxybutyl]-α,α-dimethylbenzeneacetic acid hydrochloride Method A Mix ethyl 4-[4-[4-(hydroxydiphenylmethyl)-1-piperidinyl]-1-oxobutyl]-α,α-dimethylbenzeneacetate, hydrochloride (101.92 g, 0.1807 mol) and methanol (510 mL) and stir. Rapidly add 50% sodium hydroxide (72.27 g, 0.903 mol) and wash in with water (61 mL). Heat to reflux for 2 hours, allow to cool to 35° C. and treat with sodium borohydride (3.42 g, 0.0903 mol). Add water (100 mL) and maintain at 35° C. for 10 hours. Add 37% hydrochloric acid (53.0 g) to adjust pH to 11.5. Add acetone (26.5 mL) and water (102 mL). Hold at 35° C. for 2 hours and adjust to pH 2.5 with 37% hydrochloric acid (44.69 g). Dilute with water (408 mL), cool to −15° C., stir for 1.5 hours and collect the precipitate by vacuum filtration. Wash the filtercake with deionized water (3×100 mL) and vacuum dry to give 4-[4-[4-(hydroxydiphenylmethyl)-1-piperidinyl]-1-hydroxybutyl]-α,α-dimethylbenzeneacetic acid hydrochloride hydrate (97.10 g).

Method B

Place ethyl 4-[4-[4-(hydroxydiphenylmethyl)-1-piperidinyl]-1-oxobutyl]-α,α-dimethylbenzeneacetate, hydrochloride (60.01 g, 0.106 mol) in a 1-L three necked round-bottom flask and fit the flask with a mechanical stirrer, a Claisen head, a thermometer and a reflux condenser with a nitrogen bubbler on top. Add methanol (300 mL) and turn the stirrer on. Dilute the slurry with water (60 mL) and heat to 52°–54° C. over 15–20 minutes. Hold at 52° C. for 2 hours and then add 50% sodium hydroxide (42.54 g, 0.532 mol). Heat at 73° C. for approximately 1 hour, 45 minutes, cool to less than 35° C. using a water bath and then add sodium borohydride (2.02 g, 0.0534 mol). Stir overnight at 35° C., treat with acetone (15.5 mL) and stir for 2 hours at 35° C. Acidify the mixture to a pH of 1.85 with 28% hydrochloric acid (75.72 g), dilute with water (282 mL), stir for about 30 minutes and cool over about 2 hours to −15° C. Filter the solids off and wash with water (2×75 mL) and ethyl acetate (2×75 mL). Vacuum dry the solid and allow to stand for 2 days to give 4-[4-[4-(hydroxydiphenylmethyl)-1-piperidinyl]-1-hydroxybutyl]-α,α-dimethylbenzeneacetic acid hydrochloride hydrate (Form II) (57.97 g, 91.5%) as a fine powder.

Method C

Place ethyl 4-[4-[4-(hydroxydiphenylmethyl)-1-piperidinyl]-1-oxobutyl]-α,α-dimethylbenzeneacetate (56.12 g, 0.1064 mol) in a 1-L three necked round-bottom flask and fit the flask with a mechanical stirrer, a Claisen head, a thermometer and a reflux condenser with a nitrogen bubbler on top. Add methanol (300 mL) and turn the stirrer on. Dilute the slurry with water (6 mL) and heat to reflux using a heating mantle controlled by a Therm-O-Watch. When the mixture reaches about 35° C., treat with 50% sodium hydroxide (34.05 g, 0.4256 mol) and rinse in with water (42 mL). Stir at reflux for 2 hours, 15 minutes, cool over 1 hour to 35° C. and then treat with sodium borohydride (2.02 g, 0.0534 mol). Stir for 7.5 hours and allow to stand at room temperature without stirring for 1.75 days. Warm the mixture to 35° C. and quench with acetone (15.5 mL, 0.21 mol) and stir for 2 hours. Add water (60 mL) and adjust the pH to 2.5 with 32% hydrochloric acid (65.22 g). Cool to 40° C. and rinse the pH probe with water (25 mL). Add water over about 30 minutes (192 mL), hold the temperature at 33° C. for 10 minutes and add a few seed crystals. Cool the slurry to −12° C. over about 45 minutes and isolate the solid by filtration (586.2 g). Wash with water (2×100 mL) and then with ethyl acetate (100 mL, prechilled to about −10° C.). Vacuum dry overnight (1 mmHg, 50° C.) to give 4-[4-[4-(hydroxydiphenylmethyl)-1-piperidinyl]-1-hydroxybutyl]-α,α-dimethylbenzeneacetic acid hydrochloride hydrate (Form II) (58.86 g, 98%) as a white solid.

EXAMPLE 23

Preparation of Form IV 4- [4-[4-(hydroxydiphenylmethyl) -1-piperidinyl]-1-hydroxybutyl]-α,α-dimethylbenzeneacetic acid hydrochloride (Form IV)

Place ethyl 4-[4-[4-(hydroxydiphenylmethyl)-1-piperidinyl]-1-oxobutyl]-α,α-dimethylbenzeneacetate (56.12 g, 0.1064 mol) in a 1-L three necked round-bottom flask and fit the flask with a mechanical stirrer, a Claisen head, a thermometer and a reflux condenser with a nitrogen bubbler on top. Add methanol (300 mL) and turn the stirrer on. Dilute the slurry with water (60 mL) and heat to reflux using a heating mantle controlled by a Therm-O-Watch. When the mixture reaches about 35° C., treat with 50% sodium hydroxide (34.05 g, 0.4256 mol) and rinse in with water (42 mL). Stir at reflux for 2 hours, 15 minutes, cool over 1 hour to 35° C. and then treat with sodium borohydride (2.02 g, 0.0534 mol). Stir for 7.5 hours and allow to stand at room temperature without stirring for 1.75 days. Warm the mixture to 35° C. and quench with acetone (15.5 mL, 0.21 mol) and stir for 2 hours. Add water (60 mL) and adjust the pH to 2.5 with 32% hydrochloric acid (65.22 g). Cool to 40° C. and rinse the pH probe with water (25 mL). Hold the temperature at 33° C. for 10 minutes, add a few seed crystals and add water over about 4 hours (192 mL) at 35° C. Cool the slurry to −12° C. over about 45 minutes and isolate the solid by filtration (586.2 g). Wash with water (2×100 mL) and then with ethyl acetate (100 mL, prechilled to about −10° C.). Vacuum dry overnight (1 mmHg, 50° C.) to give 4-[4-[4-(hydroxydiphenylmethyl)-1-piperidinyl]-1-hydroxybutyl]-α,α-dimethylbenzeneacetic acid hydrochloride hydrate (Form IV); mp 115°–116° C. (dec).

TABLE 18

XRPD: Table 18

| D-Space, Angstroms | Intensity, $I/I_o$, % |
|---|---|
| 10.38 | 60 |
| 6.97 | 45 |
| 6.41 | 50 |
| 5.55 | 30 |
| 5.32 | 100 |
| 5.23 | 55 |
| 5.11 | 35 |
| 4.98 | 25 |
| 4.64 | 30 |
| 4.32 | 35 |
| 4.28 | 75 |
| 4.12 | 50 |
| 4.02 | 45 |
| 3.83 | 60 |
| 3.65 | 20 |
| 3.51 | 55 |
| 3.46 | 25 |
| 2.83 | 20 |

EXAMPLE 24

Conversion of Form II to Form I 4-[4-[4-(hydroxydiphenylmethyl)-1-piperidinyl]-1-hydroxybutyl]-α,α-dimethylbenzeneacetic acid hydrochloride (Form I)

Treat 4-[4-[4-(hydroxydiphenylmethyl)-1-piperidinyl]-1-hydroxybutyl]-α,α-dimethylbenzeneacetic acid hydrochloride hydrate (Form II) (20.0 g, 0.0355 mol) with deionized water (2 g) and add acetone (60 mL) in small portions over several minutes with stirring. Filter through filter aid and wash the filter cake with acetone (30 mL). Wash the filter-cake with acetone (22 mL), reflux filtrate and then slowly add ethyl acetate (32 mL over 15 minutes) keeping the mixture at reflux. Reflux for 10 minutes, then slowly add additional ethyl acetate (23 mL over 10 minutes) and reflux for an additional 15 minutes. Add additional ethyl acetate (60 mL over 5–10 minutes) and continue refluxing for 15 minutes. Cool to approximately 8° C. in an ice bath, filter the solid and wash with ethyl acetate (85 mL). Vacuum dry at 55° C. for 1.5 hours to give the title compound (18.16 g, 95%).

EXAMPLE 25

Conversion of Form II to Form I 4-[4-[4-(Hydroxydiphenylmethyl)-1-piperidinyl]-1-hydroxybutyl]-α,α-dimethylbenzeneacetic acid hydrochloride Method A Treat 4-[4-[4-(hydroxydiphenylmethyl)-1-piperidinyl]-1-hydroxybutyl]-α,α-dimethylbenzeneacetic acid hydrochloride hydrate (Form II) (5.00 g, 0.0083 mol) with methylethyl ketone (130 mL). Slowly add water (0.4 mL), filter through filter aid and wash the filter cake with methylethyl ketone (20 mL). Heat to reflux and distill off 75 mL of solvent, cool to −15° C. and collect by vacuum filtration. Wash with methylethyl ketone (2×10 mL) and vacuum dry at 60° C. to give the title compound (4.33 g, 97%); mp 196°–198° C.

Method B

Treat 4-[4-[4-(hydroxydiphenylmethyl)-1-piperidinyl]-1-hydroxybutyl]-α,α-dimethylbenzeneacetic acid hydrochloride hydrate (Form II) (1.4 g) with acetone (60 mL) and heat to reflux. Reduce the volume to approximately 35 mL to remove all water which boils off as an azeotrope (88/12:acetone/water). Cool the solution and collect the title compound as a crystalline solid.

Method C

Mix 4-[4-[4-(hydroxydiphenylmethyl)-1-piperidinyl]-1-hydroxybutyl]-α,α-dimethylbenzeneacetic acid hydrochloride hydrate (Form II) (53.88 g, 0.100 mol) and add water (4.79 g) and methyl ethyl ketone (240 mL). Stir until the solid is slurried up and add additional methyl ethyl ketone (1 L). Stir for 0.5 hours, filter through a pad of filter aid, wash the filtercake with methyl ethyl ketone (100 mL) and transfer the filtrate and wash to a 2 L, 3-necked flask fitted with a thermometer, mechanical stirrer and distillation head. Distill off a total of 721 mL of methyl ethyl ketone, cool and stir over 1 hour to 40° C. Cool to −15° C. and hold for 10 minutes. Collect the solid by vacuum filtration and wash the filtercake with methyl ethyl ketone (2×65 mL) and vacuum dry at 55° C. overnight to give the title compound (52.76 g, 97.9%); mp 197.5°–200° C.

Method D

Treat 4-[4-[4-(hydroxydiphenylmethyl)-1-piperidinyl]-1-hydroxybutyl]-α,α-dimethylbenzeneacetic acid hydrochloride hydrate (Form II) (40.0 g, 0.0696 mol, assayed at 93.6% purity, having 0.89 g water present and 35.1 g, 0.0575 mol, assayed at 88.0% purity, having 2.47 g water present) with water (8.30 g; the amount calculated to bring the weight of water present to 17% of the anhydrous weight of 4-[4-[4-(hydroxydiphenylmethyl)-1-piperidinyl]-1-hydroxybutyl]-α,α-dimethylbenzeneacetic acid hydrochloride hydrate, taking into account the water in the hydrated salt). Add methyl ethyl ketone (approximately 500 mL) and stir until most of the solids dissolve. Add additional methyl ethyl ketone (700 mL) in portions over approximately 10 minutes and continue stirring for ½ hour. Filter through a thin pad of filter aid, wash the filtercake and flask with additional methyl ethyl ketone (100 mL) and transfer to a boiling flask fitted with a thermometer, mechanical stirrer, heating mantle, a 12-plate Oldershaw (vacuum-jacketed) distillation column and a distillation head with the capability of regulating the reflux ratio in a rough fashion, washing in with additional methyl ethyl ketone (100 mL). Distill off 450 mL of solvent, cool to −15° C. and filter the solid. Wash with methyl ethyl ketone (2×100 mL) and dry to give the title compound (68.3 g, 99.9%); mp 197°–199° C.

Method E

Bring methyl ethyl ketone (4 mL) to a boil and add 4-[4-[4-(hydroxydiphenylmethyl)-1-piperidinyl]-1-hydroxybutyl]-α,α-dimethylbenzeneacetic acid hydrochloride (500 mg). Decant the top layer and add methyl ethyl ketone (3 mL) to the aqueous layer. Boil the solution until the temperature reached 79° C., reduce the volume by 25%, remove from heat and cover with aluminum foil. Allow the solution to cool, filter the resulting crystals and air dry to give the title compound.

EXAMPLE 26

Conversion of Form I to Form II 4-[4-[4-(Hydroxydiphenylmethyl)-1-piperidinyl]-1-hydroxybutyl]-α,α-dimethylbenzeneacetic acid hydrochloride hydrate Method A Treat 4-[4-[4-(hydroxydiphenylmethyl)-1-piperidinyl]-1-hydroxybutyl]-α,α-dimethylbenzeneacetic acid hydrochloride (Form I) (2.0 g) with ethanol (4 mL) and deionized water (20 mL). Heat at 80° C. until a solution is formed and then stir at room temperature for 23 hours. Filter the resulting slurry, wash with water (2×10 mL) and dry under vacuum at 35° C. overnight to give the title compound (1.88 g); mp 100°–105° C.

TABLE 19

XRPD: Table 19

| D-Space, Angstroms | Intensity, I/I$_o$, % |
| --- | --- |
| 11.41 | 20 |
| 7.98 | 20 |
| 7.83 | 45 |
| 6.58 | 45 |
| 6.42 | 60 |
| 5.66 | 20 |
| 5.52 | 45 |
| 5.39 | 30 |
| 5.23 | 65 |
| 5.14 | 45 |
| 4.86 | 65 |
| 4.72 | 100 |
| 4.45 | 65 |
| 4.40 | 45 |
| 4.32 | 45 |
| 4.18 | 45 |
| 4.06 | 65 |
| 4.02 | 55 |
| 3.85 | 25 |
| 3.79 | 75 |
| 3.74 | 95 |
| 3.61 | 80 |
| 3.56 | 25 |
| 3.47 | 65 |
| 3.41 | 20 |
| 2.74 | 20 |

Method B

Mix water (35.5 mL), methanol (26.3 mL) and sodium chloride (2.59 g). Add 4-[4-[4-(hydroxydiphenylmethyl)-1-piperidinyl]-1-hydroxybutyl]-α,α-dimethylbenzeneacetic acid hydrochloride (Form I) (4.77 g). Heat to reflux on a steam bath until dissolution and cool to −10° C. Filter the resulting solid, wash with water (2×25 mL) and vacuum dry overnight to give the title compound (4.80 g).

EXAMPLE 27

Conversion of Form II into Form III 4-[4-[4-(Hydroxydiphenylmethyl)-1-piperidinyl]-1-hydroxybutyl]-α,α-dimethylbenzeneacetic acid hydrochloride (Form III)

Place 4-[4-[4-(Hydroxydiphenylmethyl)-1-piperidinyl]-1-hydroxybutyl]-α,α-dimethylbenzeneacetic acid hydrochloride hydrate (Form II) (55.56 g, 0.0929 mol having 10% water) in a pressure bottle along with water (2.96 g) and acetone (38.1 g). Seal the bottle tightly and heat to approximately 80° C. Cool to about 50° C., filter through filter aid in a coarse sintered glass funnel and dilute with acetone (90 g). Transfer to a 1 L flask fitted with a mechanical stirrer, thermometer and a reflux condenser. Heat the mixture to reflux and allow to cool and stir over the weekend. Cool to −15° C. and filter on a coarse sintered glass funnel, wash with ethyl acetate (2×50 mL) and vacuum dry at 50° C.

Place a majority of the solid obtained (45.24 g) in a 500 mL three necked flask fitted with a mechanical stirrer, thermometer and a reflux condenser. Add acetone (240 mL) and water (4.82 g) and reflux the mixture overnight. Allow the slurry to cool to 35° C. and place in an ice water bath and cool to less then 5° C. Filter the solid off on a coarse sintered glass funnel, wash with ethyl acetate (50 mL) and vacuum dry at 50° C. for several hours to give the title compound as a white crystalline powder (43.83 g, 97%); mp 166.5–170.5° C.

TABLE 20

XRPD: Table 20

| D-Space, Angstroms | Intensity, $I/I_o$, % |
|---|---|
| 8.95 | 95 |
| 4.99 | 20 |
| 4.88 | 100 |
| 4.75 | 35 |
| 4.57 | 25 |
| 4.47 | 25 |
| 4.46 | 20 |
| 3.67 | 20 |
| 3.65 | 25 |

EXAMPLE 28

Conversion of Form III into Form I 4-[4-[4-(Hydroxydiphenylmethyl)-1-piperidinyl]-1-hydroxybutyl]-α,α-dimethylbenzeneacetic acid hydrochloride (Form I)

Place 4-[4-[4-(Hydroxydiphenylmethyl)-1-piperidinyl]-1-hydroxybutyl]-α,α-dimethylbenzeneacetic acid hydrochloride (Form III) (40.0 g as an ethyl acetate wetcake-27.9 g dry basis) in a 1 L three necked flask fitted with a mechanical stirrer, thermometer and a reflux condenser. Add acetone (240 mL) and heat the mixture to reflux for about 20 hours. Cool the slurry to −15° C. and isolate the solids by filtration on a coarse sintered glass frit funnel. Wash with ethyl acetate (50 mL) and vacuum dry overnight to give the title compound (26.1 g, 93.7%); mp 197.5–199.5° C.

TABLE 21

XRPD: Table 21

| D-Space, Angstroms | Intensity, $I/I_o$, % |
|---|---|
| 11.75 | 35 |
| 7.23 | 35 |
| 6.24 | 60 |
| 5.89 | 40 |
| 5.02 | 20 |
| 4.94 | 30 |
| 4.83 | 100 |
| 4.44 | 30 |
| 3.93 | 75 |
| 3.83 | 20 |
| 3.77 | 85 |
| 3.71 | 25 |
| 3.62 | 30 |
| 3.32 | 25 |
| 3.31 | 20 |

EXAMPLE 29

Conversion of Form IV into Form I 4-[4-[4-(Hydroxydiphenylmethyl)-1-piperidinyl]-1-hydroxybutyl]-α,α-dimethylbenzeneacetic acid hydrochloride (Form I)

Place 4-[4-[4-(hydroxydiphenylmethyl)-1-piperidinyl]-1-hydroxybutyl]-α,α-dimethylbenzeneacetic acid hydrochloride hydrate (Form IV) (54.35 g, 0.0970 mol, having 4% water present) in a pressure bottle along with water (4.16 g) and acetone (38.1 g). Seal the bottle tightly and heat to approximately 80° C. Cool to less then 60° C., filter through filter aid in a coarse sintered glass funnel and rinse the filter cake with acetone (32.4 g). Place acetone (215 g) in a 1 L three necked flask fitted with a mechanical stirrer, thermometer, a reflux condenser and containing a small amount of Form I crystals and heat to reflux. Add a portion of the acetone/water solution of 4-[4-[4-(hydroxydiphenylmethyl)-1-piperidinyl]-1-hydroxybutyl]-α,α-dimethylbenzeneacetic acid hydrochloride hydrate (Form IV) (47.65 g) to the refluxing acetone over about 10 minutes. Slowly add ethyl acetate (157.5 g) over 45 minutes then add the remaining portion of the acetone/water solution of 4-[4-[4-(hydroxydiphenylmethyl)-1-piperidinyl]-1-hydroxybutyl]-α,α-dimethylbenzeneacetic acid hydrochloride hydrate (Form IV), rinsed in with about 20 mL of acetone. Add additional ethyl acetate (157.5 g) over 45 minutes to 1 hour, maintaining the slurry at reflux. Stir for 15 minutes, cool to −15° C. and vacuum filter the white solid on a 350 mL coarse sintered glass funnel. Wash the solids with ethyl acetate (2×50 mL) and vacuum dry overnight to give the title compound (50.36 g, 97%); mp 198–199.5° C.

TABLE 22

XRPD: Table 22

| D-Space, Angstroms | Intensity, $I/I_o$, % |
|---|---|
| 14.89 | 20 |
| 11.85 | 20 |
| 7.30 | 20 |
| 6.28 | 70 |
| 5.91 | 25 |
| 5.55 | 20 |
| 5.05 | 25 |
| 4.96 | 55 |
| 4.85 | 100 |
| 4.57 | 45 |
| 4.45 | 55 |
| 3.94 | 45 |
| 3.89 | 20 |
| 3.84 | 20 |
| 3.78 | 60 |
| 3.72 | 35 |
| 3.63 | 20 |
| 3.07 | 20 |
| 3.04 | 20 |
| 2.45 | 20 |

Utilizing the procedures described in the previous examples, the corresponding tablets and capsules may be prepared from Form I anhydrous 4-[4-[4-(Hydroxydiphenylmethyl)-1-piperidinyl]-1-hydroxybutyl]-α,α-dimethylbenzeneacetic acid hydrochloride, Form III anhydrous 4-[4-[4-(Hydroxydiphenylmethyl)-1-piperidinyl]-1-hydroxybutyl]-α,α-dimethylbenzeneacetic acid hydrochloride or various mixtures thereof. In addition, utilizing the procedures described in the previous examples, the corresponding tablets and capsules may be prepared from Form II hydrated 4-[4-[4-(Hydroxydiphenylmethyl)-1-piperidinyl]-1-hydroxybutyl]-α,α-dimethylbenzeneacetic acid hydrochloride, Form IV hydrated 4-[4-[4-(Hydroxydiphenylmethyl)-1-piperidinyl]-1-hydroxybutyl]-α,α-dimethylbenzeneacetic acid hydrochloride or various mixtures thereof. It is readily appreciated by one of ordinary skill in the art that during the formulation process of the tablets and capsules described in the preceding examples, interconversion between the above described polymorphs and pseudomorphs of 4-[4-[4-(Hydroxydiphenylmethyl)-1-piperidinyl]-1-hydroxybutyl]-α,α-dimethylbenzeneacetic acid hydrochloride may occur. In addition, it is understood that the resulting tablet or capsule may contain various mixtures of Forms I, II, III and IV of 4-[4-[4-(Hydroxydiphenylmethyl)-1-piperidinyl]-1-hydroxybutyl]-α,α-dimethylbenzeneacetic acid hydrochloride, hydrated and anhydrous.

What is claimed is:

1. A pharmaceutical composition in solid unit dosage form prepared by a process comprising, blending together a compound of the formula;

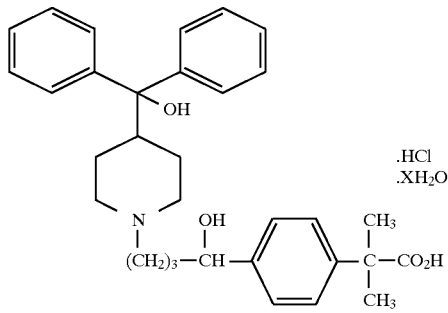

wherein X is a number ranging from about zero to 5, and the individual optical isomers thereof, with microcrystalline cellulose, lactose and pregelatinized starch; adding a solution of gelatin in water with mixing; drying and milling the mixture; and adding croscarmellose sodium with mixing.

2. A pharmaceutical composition in solid unit dosage form according to claim 1 wherein the microcrystalline cellulose, lactose, pregelatinized starch, gelatin and croscarmellose sodium are combined in amounts of about 33.8%, 33.8%, 9.6%, 3.5% and 4.8%, respectively, by weight of the composition.

3. A pharmaceutical composition in solid unit dosage form according to claim 1 wherein the microcrystalline cellulose, lactose, pregelatinized starch, gelatin, and croscarmellose sodium are combined in amounts of about 33.7%, 33.7%, 9.6%, 3.5%, and 4.8%, respectively, by weight of the composition.

4. A pharmaceutical composition in solid unit dosage form prepared by a process comprising blending together a compound of the formula;

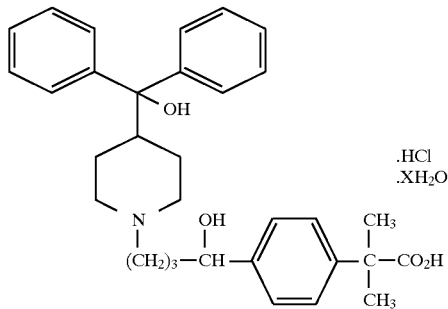

wherein X is a number ranging from about zero to 5, and the individual optical isomers thereof, with microcrystalline cellulose, lactose and pregelatinized starch; adding a solution of gelatin in water with mixing; drying and milling the granulated mixture; adding croscarmellose sodium with mixing; and adding magnesium stearate with mixing.

5. A pharmaceutical composition in solid unit dosage form according to claim 4 wherein the final mixture is pressed into tablets.

6. A pharmaceutical composition in solid unit dosage form according to claim 4 wherein the microcrystalline cellulose, lactose, pregelatinized starch, gelatin, croscarmellose sodium and magnesium stearate are combined in amounts of about 33.7%, 33.7%, 9.6%, 3.5%, 4.8% and 0.5%, respectively, by weight of the composition.

7. A pharmaceutical composition in solid unit dosage form, comprising;
   a) a therapeutically effective amount of a piperidinoalkanol compound or a pharmaceutically acceptable salt thereof wherein said piperidinoalkanol compound is of the formula:

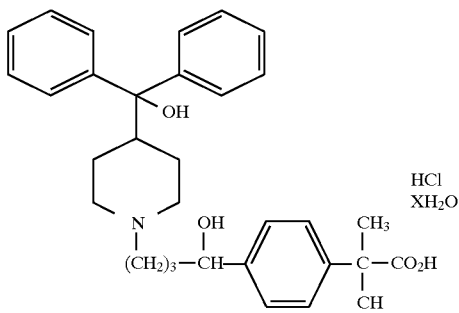

wherein X is a number ranging from about zero to 5, and the individual optical isomers thereof; and
   b) croscarmellose sodium, microcrystalline cellulose, lactose, pregelatinized starch and gelatin in amounts of about 1% to about 10%, 20% to about 85%, 20% to about 85%, 1% to about 30% and 1% to about 15%, respectively, by weight of the composition.

8. The pharmaceutical composition in solid unit dosage form according to claim 7 wherein croscarmellose sodium, microcrystalline cellulose, lactose, pregelatinized starch and gelatin are present in amounts of about 4.8%, 33.8%, 33.8%, 9.6% and 3.5%, respectively, by weight of the composition.

9. A pharmaceutical composition in solid unit dosage form, comprising;
   a) a therapeutically effective amount of a piperidinoalkanol compound or a pharmaceutically acceptable salt thereof wherein said piperidinoalkanol compound is of the formula:

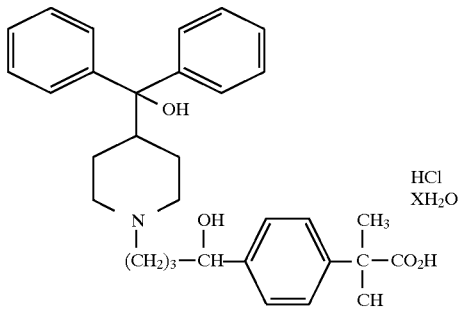

wherein X is a number ranging from about zero to 5, and the individual optical isomers thereof; and
   b) croscarmellose sodium, microcrystalline cellulose, lactose, pregelatinized starch, gelatin and magnesium stearate in amounts of about 1% to about 10%, 20% to about 85%, 20% to about 85%, 1% to about 30%, 1% to about 15% and 0.05% to about 3.0%, respectively, by weight of the composition.

10. The pharmaceutical composition in solid unit dosage form according to claim 9 wherein croscarmellose sodium, microcrystalline cellulose, lactose, pregelatinized starch, gelatin and magnesium stearate are present in amounts of about 4.8%, 33.7%, 33.7%, 9.6%, 3.5% and 0.5%, respectively, by weight of the composition.

11. The pharmaceutical composition in solid unit dosage form according to claim 9 wherein croscarmellose sodium, microcrystalline cellulose, lactose, pregelatinized starch, gelatin and magnesium stearate are present in amounts of about 4.8%, 25.7%, 25.7%, 9.6%, 3.5% and 0.75%, respectively, by weight of the composition.

12. A pharmaceutical composition in solid unit dosage form, comprising;
   a) a therapeutically effective amount of a piperidinoalkanol compound or a pharmaceutically acceptable salt thereof wherein said piperidinoalkanol compound is of the formula:

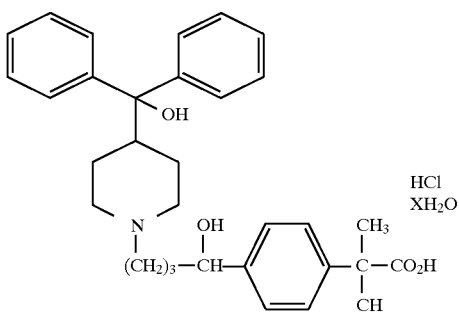

wherein X is a number ranging from about zero to 5, and the individual optical isomers thereof; and
   b) croscarmellose sodium, microcrystalline cellulose, pregelatinized starch, and magnesium stearate in amounts of about 1% to about 10%, 20% to about 85%, 5% to about 50% and 0.05% to about 3%, respectively, by weight of the composition.

13. The pharmaceutical composition in solid unit dosage form according to claim 12 wherein croscarmellose sodium, microcrystalline cellulose, pregelatinized starch, and magnesium stearate are present in amounts of about 6%, 33.3%, 30% and 0.75%, respectively, by weight of the composition.

14. The pharmaceutical composition in solid unit dosage form according to claim 4 wherein the microcrystalline cellulose, lactose, pregelatinized starch, gelatin, croscarmellose sodium and magnesium stearate are combined in amounts of about 33.8%, 33.8%, 9.6%, 3.5%, 4.8% and 0.5%, respectively, by weight of the composition.

15. The pharmaceutical composition according to claim 1 wherein X is zero.

16. The pharmaceutical composition according to claim 2 wherein X is zero.

17. The pharmaceutical composition according to claim 4 wherein X is zero.

18. The pharmaceutical composition according to claim 14 wherein X is zero.

19. The pharmaceutical composition according to claim 7 wherein X is zero.

20. The pharmaceutical composition according to claim 8 wherein X is zero.

21. The pharmaceutical composition according to claim 9 wherein X is zero.

22. The pharmaceutical composition according to claim 10 wherein X is zero.

23. The pharmaceutical composition according to claim 11 wherein X is zero.

24. The pharmaceutical composition according to claim 12 wherein X is zero.

25. The pharmaceutical composition according to claim 13 wherein X is zero.

* * * * *